US009358211B2

(12) United States Patent
Akala et al.

(10) Patent No.: US 9,358,211 B2
(45) Date of Patent: Jun. 7, 2016

(54) STEALTH POLYMERIC PARTICLES FOR DELIVERY OF BIOACTIVE OR DIAGNOSTIC AGENTS

(71) Applicant: Howard University, Washington, DC (US)

(72) Inventors: Emmanuel Oyekanmi Akala, Mitchellville, MD (US); Oluyomi Modupe Okunola, Beltsville, MD (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/292,314

(22) Filed: May 30, 2014

(65) Prior Publication Data
US 2014/0274929 A1  Sep. 18, 2014

Related U.S. Application Data

(62) Division of application No. 12/952,856, filed on Nov. 23, 2010, now Pat. No. 8,772,355.

(51) Int. Cl.
| A61K 9/16 | (2006.01) |
| A61K 31/135 | (2006.01) |
| A61K 31/337 | (2006.01) |
| A61K 31/704 | (2006.01) |
| C08F 220/68 | (2006.01) |
| C08F 8/00 | (2006.01) |
| C08F 8/30 | (2006.01) |
| A61K 9/51 | (2006.01) |
| C08F 290/06 | (2006.01) |

(52) U.S. Cl.
CPC ............. *A61K 9/1641* (2013.01); *A61K 9/5146* (2013.01); *A61K 31/135* (2013.01); *A61K 31/337* (2013.01); *A61K 31/704* (2013.01); *C08F 8/00* (2013.01); *C08F 8/30* (2013.01); *C08F 220/68* (2013.01); *C08F 290/062* (2013.01); *Y10T 428/2982* (2015.01)

(58) Field of Classification Search
CPC . A61K 9/1641; A61K 31/337; A61K 31/135; A61K 31/704; C08F 220/68
USPC ......... 514/34, 449, 657; 526/211, 215, 219.6, 526/320
See application file for complete search history.

(56) References Cited

U.S. PATENT DOCUMENTS

| 4,346,183 | A | * | 8/1982 | Hyde ............................. 523/200 |
| 5,130,479 | A | | 7/1992 | Ulbrich |
| 6,828,025 | B2 | | 12/2004 | Ali |
| 7,358,302 | B2 | * | 4/2008 | Matsumoto et al. ............. 525/50 |
| 2002/0064513 | A1 | | 5/2002 | Maitra |
| 2003/0018128 | A1 | | 1/2003 | Wang |
| 2005/0169957 | A1 | | 8/2005 | Hossainy |

FOREIGN PATENT DOCUMENTS

| WO | 2005025736 | 3/2005 |
| WO | 2007074476 | 7/2007 |

OTHER PUBLICATIONS

Torchilin VP. Micellar Nanocarriers: Pharmaceutical Perspectives. Pharmaceut Res 24:1-16, 2007.*
Chan et al. Acid-cleavable polymeric core—shell particles for delivery of hydrophobic drugs. Journal of Controlled Release 115 (2006) 197-207.*
Achilias, Dimitris S, and Irini D. Sideridou, Kinetics of the benzoyl peroxide/amine initiated free-radical polymerization of dental dimethacrylate monomers: Experimental studies and mathematical modeling for TEGDMA and bis-EMA, Macromolecules, 37, 4254-65 (2004).
Akala, Emmanuel O, Oluchi Elekwachi, Vantoria Chase, Hausalynn Johnson, Marjorie Lazarre, Kenneth Scott, Organic redox-initiated polymerization process for the fabrication of hydrogels for colon-specific drug delivery, Drug Development and Industrial Pharmacy, 29(4), 375-386 (2003).
Akala, Emmanuel O., Pavia Kopeckova, Jindrich Kopecek, Novel pH-sensitive hydrogels with adjustable swelling kinetics; Biomaterials, 19, 1037-47 (1998).
Al-Ghananeem, Abeer M., Malkawi Ahmad H., Muammer Yahya, Balko Justin M., Black Esther P., Mourad Walid and Romond Edward, Intratumoral Delivery of Paclitaxel in Solid Tumor from Biodegradable Hyaluronan Nanoparticle Formulations, AAPS Pharm. Sci. Tech., 10(2), 410-417 (2009).
Allemann Eric, Eric Doelker and Robert Gurny, Drug loaded Poly(lactic acid) nanoparticles produced by a reversible salting out process: Purification of an injectable dosage form, European Journal of Pharmaceutics and Biopharmaceutics, 39(1), 13-18 (1993).
Athanasiou, Kyriacos A., C. Mauli Agrawal, F. Alan Barber and Stephen S. Burkhart, Orthopaedic applications for PLA- PGA biodegradable polymers, The Journal of Arthroscopy and Related Surgery, 14(7), 726-737 (1998).
Bakare, O., Ashendel, C. L, Peng, H., Zalkow, L H., Burgess, E. M., Synthesis of MEK1 Inhibitory Activities of Imido- Substituted 2-Chloro-1 ,4-naphthoquinones, Bioorganic & Medicinal Chemistry 11, 3165-70 (2003).
Bamnolker, H., Margel, S., Dispersion Polymerization of Styrene in Polar Solvent: Effect of Reaction parameters onMicrosphere Surface Composition and Surface Properties, Size and Size Distribution, and Molecular Weight, Journal of Polymer Science: Part A: Polymer Chemistry 34, 1857-71 (1996).
Boffa, Lisa S, and Bruce M. Novak, Link-Functionalized Polymers: An unusual macromolecular architecture through bifunctional initiation, Macromolecules, 30, 3494-3506 (1997).

(Continued)

*Primary Examiner* — Clinton Brooks
*Assistant Examiner* — Yih-Horng Shiao
(74) *Attorney, Agent, or Firm* — Fitch, Even, Tabin & Flannery, LLP

(57) ABSTRACT

The present invention is directed to a crosslinked or non-crosslinked polymer particle, wherein the crosslinked polymer particle comprises a copolymer of poly(alkylene glycol-graft-acrylate) that is crosslinked by at least one hydrolysable monomer or crosslinking agent. The present invention is also directed to a polymer particle comprising a crosslinked polymer particle that is a product of starting materials comprising (a) a hydrophilic monomer, (b) a hydrophobic monomer, and (c) a hydrolysable crosslinking agent (the crosslinking agent may be absent in the case of non-crosslinked particles). The present invention is still further directed to a polymer particle comprising a crosslinked copolymer, where the crosslinked copolymer includes structures represented by Formulas (I), (II), and (III), as defined in the specification. Other embodiments of the present invention also include methods of manufacturing polymer particles.

20 Claims, 18 Drawing Sheets

(56) References Cited

OTHER PUBLICATIONS

Burm, J.-P., Jhee, S. S., Chin, A., Moon, Y. S. K., Jeong, E., Nii, L., Fox, J. L., Gill, M.A., Stability of Paclitaxel with Ondansetron Hydrochloride or Ranitidine Hydrochloride During Simulated Y-Site Administration, American Journal of Hospital Pharmacy 51, 1201-1204 (1994).
Cadee, J. A, M. De Kerf, C. J. De Groot, W. Den Otter, W. E. Hennink, Synthesis, characterization of 2-(mathacryloyloxy)-(di-) L-lactate and their application in dextran-based hydrogels, Polymer, 40, 6877-81 (1999).
Cammas, S., Suzuki, K.; Sane, C.; Sakurai, Y., Kataoka, K., Okano, T, Thermo-Responsive polymer nanoparticles with a Core-Shell Micelle Structure as Site-Specific Drug Carriers, Journal of Controlled Release 48, 157-64 (1997).
Cancer Nanotechnology (Going Small for Big Advances: Using Nanotechnology to Advance Cancer Diagnosis, Prevention and Treatment). U.S. Department of Health and Human Services, National Institutes of Health/National Cancer Institute. NIH Publication No. 04-5489, (2004).
Capek, Ignac, Surface active properties of polyoxyethylene macromonomers and their role in radical polymerization in disperse systems, Advances in Colloid and Interface Science, 88(3), 295-357 (2000).
CellTiter.RTM.-Glo Luminescent Cell Viability Assay Technical Bulletin, TB 288, Jun. 2009, Promega Corporation, WI, USA.
Chavanpatil, Mahesh D., Patil Yogesh and Panyam Jayanth, Susceptibility of nanoparticle-encapsulated paclitaxel to P-glycoprotein-mediated drug efflux, International Journal of Pharmaceutics, 320, 150-156 (2006).
Couvreur, Patrick and Christine Vauthier, Nanotechnology: Intelligent design to treat complex disease, Pharmaceutical Research, 23(7), 1417-50 (2006).
Czelusniak, Izabela, Ezat Khosravi, Alan M. Kenwright, Christopher W. G. Ansell, Synthesis, Characterization, and Hydrolytic Degradation of Polylactide-Functionalized Polyoxanorbornenes, Macromolecules, 40, 1444-52 (2007).
Danhier, Fabienne et al., Paclitaxel-loaded PEGylated PLGA-based Nanoparticles: In Vitro and In Vivo Evaluation. Journal of Controlled Release, 133 (2009) pp. 11-17.
Eguiburu, Jose Luis, Maria Fernandez Berridi and Julio San Roman, Functionalization of poly(L-lactide) macromonomers by ring-opening polymerization of L-lactide initiated with hydroxyethyl methacrylate-aluminium alkoxides, Polymer, 36(1), 173-179 (1995).
Errico, Cesare, Bartoli Cristina, Chiellini Federica and Chiellini Emo, Poly(hydroxyalkanoates)-based Polymeric Nanoparticles for Drug Delivery, Journal of Biomedicine and Biotechnology, 2009, Article ID 571702, 1-10 pages (2009).
European Patent Office Extended European Search Report dated May 21, 2014 for European Application No. 11842912.5, 6 pages.
Feng, S.-S., Chien, S., Chemotherapeutic Engineering: Application and Further Development of Chemical Engineering Principles for Chemotherapy of Cancer and Other Diseases, Chemical Engineering Science 58, 4087-4114 (2003).
Ferrari, M. Cancer Nanotechnology: Opportunities and Challenges, Nature Reviews/Cancer, 5; 1-11 (2005).
Gaither, A., Lourgenko, V., RNA Interference Technologies and their Use in Cancer Research, Curr. Opin. Oneal., 19:50-54 (2007).
Gerhardt, Warren W., David E. Noga, Kenneth I. Hardcastle, Andres J. Garcia, David M. Collard, Marcus Weck, Functional Lactide Monomers: Methodology and Polymerization, Biomacromolecules, 7, 17-1742 (2006).
Gref. R., A. Domb, P. Quellec, T. Blunk, R. H. Muller, J. M. Verbavatz, R. Langer, The controlled intravenous delivery of drugs using PEG-coated sterically stabilized nanospheres, Advanced Drug Delivery Reviews, 16, 215-33 (1995).
Herault, Damien, Christine Saluzzo, Marc Lemaire, Preparation of monodisperse enantiomerically pure glycidyl methacrylate-ethylene glycol dimethacrylate copolymers in dispersion copolymerization: Functionalization, Reactive and Functional Polymers, 66, 567-77 (2006).
Horak, Daniel, Effect of reaction parameters on the particle size in the dispersion polymerization of 2-Hydroxyethyl Methacrylate, Journal of Polymer Science Part A: Polymer Chemistry, 37, 3785-92 (1999).
Horak, Daniel, et al., Poly(2-hydroxyethyl methacrylate)-based slabs as a mouse embryonic stem cell support, Biomaterials 25 (2004) 5249-5260.
Horak, Daniel and Ostap Chaykivskyy, Poly (2-Hydroxyethyl Methacrylate-co-N,O-Dimethacryloylhydroxylamine) particles by dispersion polymerization, Journal of Polymer Science: Part A: Polymer Chemistry, 40, 1625-1632 (2002).
Huang, S. K., Stauffer, P. R., Hong, K., Uuo, J. W. H., Philips, T. L, Huang, A., Papahadjopoulos, D., Liposomes and Hyperthermia in Mice: Increased Tumor Uptake and Therapeutic Efficacy of Doxorubicin in Sterically Stabilized Liposomes, Cancer Research 54, 2186-91 (1994).
Huang, Samuel J. and John M. Onyari, Multicomponent polymers of poly(lactic acid) macromonomers with methacrylate terminal and copolymers of poly(2-hydroxyethyl methacrylate), Journal of Macromolecular Science—Pure and Applied Chemistry A, 33(5), 571-84 (1996).
Iojoiu, Christina, David Cade, Hatem Fessi and Thierry Hamaide, Synthesis of oligocaprolactone vinyl ether macromonomers and their use for indomethacin encapsulation in polymer nanoparticles based on polycaprolactone macromonomer-maleic anhydride-N-vinyl pyrrolidone terpolymers, Polymer International, 55, 222-28 (2006).
Jin Cheng, Bai Ling, Wu Hong, Song Wenjie, Guo Guohen and Dou Kefeng, Cytotoxicity of PaclitaxelIncorporated in PLGA Nanoparticles on Hypoxic Human Tumor Cells, Pharmaceutical Research, 26(7), 1776-1784 (2009).
Kawaguchi, S., Winnik, M.A., Ito, K., Dispersion Copolymerization of n-Butyl Methacrylate with Poly(ethylene oxide) Macromonomers in Methanol-Water: Comparison of Experiment with Theory, Macromolecules 28, 1159-66 (1995).
Kawaguchi, Seigou and Koichi Ito, Dispersion Polymerization, Advances in Polymer Science, 175, 299-328 (2005).
Kim, Jin-Woong, Chung-Hyuk Lee, Jung Bae Jun, Kyung-Do Suh, Monodisperse micron-sized crosslinked polystyrene particles: VII. Importance of monomer-diffusible surface characteristics of growing particles, Colloids and Surfaces A: Physicochemical and Engineering Aspects, 194, 57-64 (2001).
Kim, Mi Sun, Gyu Ho Lee, Jae-Min Hong, Hyunjung Lee, Synthesis of Monodisperse PS-co-PDMS Microspheres by Dispersion Polymerization, Materials Science and Engineering C, 27, 1247-51 (2007).
Kim, So Yeon, I L Gyun Shin, Young Moo Lee, Chong Su Cho, Yong Kiel Sung, Methoxy poly(ethylene glycol) and .epsilon.-caprolactone amphiphilic block copolymeric micelle containing indomethacin. II. Micelle formation and drug release behaviours, Journal of Controlled Release, 51, 13-22 (1998).
Kricheldorf, Hans R., Kreiser-Saunders and Caroline Boettcher, Polylactones: 31. Sn(II)octoate-initiated polymerization of L-lactide: a mechanistic study, Polymer, 36(6), 1253-59 (1995).
Kunzmann, Andrea, Andersson Britta, Thurnherr Tina, Krug Harald, Scheynius Annika, Fadeel Bengt, Toxicology of engineered nanomaterials: Focus on biocompatibility, biodistribution and biodegradation, Biochimica et Biophysica Acta, 1810:361-373, (2011). (e-published ahead of printing: (May 8, 2010).
Langer, Robert, Polymer-Controlled Drug Delivery Systems, Accounts of Chemical Research, 26(10), 537-42 (1993).
Lasic, D. D., Martin, F. J., Gabizon, A., Huang, S. K., Papahadjopoulos, D., Sterically Stabilized Liposomes: A Hypothesis on the Molecular Origin of the Extended Circulation Times, Biochimica et Biophysica Acta (BBA)—Biomembranes 1070, 187-92 (1991).
Layre, A., P. Couvreur, H. Chacun, J. Richard, C. Passirani, D. Requier, J. P. Benoit, R. Gref, Novel composite core—shell nanoparticles as busulfan carriers, Journal of Controlled Release, 111, 271-80 (2006).
Leobandung, William, Hideki Ichikawa, Yoshinobu Fukumori, Nicholas A. Peppas, Monodisperse Nanoparticles of Poly(ethylene glycol) Macromers and N-Isopropyl Acrylamide for Biomedical Applications. Journal of Applied Polymer Science, 87, 1678-84 (2003).

(56) References Cited

OTHER PUBLICATIONS

Longnecker, S. M., Donehower, R. C., Cates, A. E., Chen, T.-L., Brundrett, R. B., Grochow, L. B., Ettinger, D. S., Colvin, M., High-Performance Liquid Chromatography Assay for Taxol in Human Plasma and Urine and Pharmacokinetics in a Phase I Trial, Cancer Treatment Reports 71, 53-59 (1987).
Luo Weijun, Suming Li, Jianzhong Bei, Shenguo Wang, Synthesis and Characterization of Poly(L-lactide)-Poly(ethylene glycol) Multiblock Copolymers, Journal of Applied Polymer Science, 84, 1729-36 (2002).
McGee, J. Paul, Stanley S. Davis, Derek T. O'Hagan, Zero order release of protein from poly (D,L-lactide-co-glycolide) microparticles prepared using a modified phase separation technique, Journal of Controlled Release, 34, 77-86 (1995).
Merkli, A., C. Tabatabay, R. Gurny, J. Heller, Biodegradable polymers for the controlled release of ocular drugs, Progress in Polymer Science, 23, 563-80 (1998).
Metters, A. T., K. S. Anseth, C. N. Bowman, Fundamental studies of a novel, biodegradable PEG-b-PLA hydrogel, Polymer, 41, 3993-4004 (2000).
Minko, T., Dharap, S. S., Pakunlu, R. 1., Wang, Y., Molecular Targeting of Drug Delivery Systems to Cancer, Current Drug Targets, 5, 389-406 (2004).
Nair, S. Lakshmi and Cato T. Laurencin, Biodegradable polymers as biomaterials, Progress in Polymer Science, 32, 762-98 (2007).
Nasongkla, Norased, Bey, Erik, Ren, Jimin, Ai, Hua, Khemtong, Chalermchai, Guthi, Jagadeesh Setti, Chin, Shook-Fong, Sheery, A. Dean, Boothman, David A. and Gao, Jinming, Multifunctional Polymeric Micelles as Cancer-Targeted, MRI-Uitasenstive Drug Delivery Systems, Nano Letters, 6(11), 2427-2430 (2006).
Nugroho, M. B., Kawaguchi, S., Ito, K., Winnik, M. A, Control of Particle Size in Dispersion Polymerization Using Poly (ethylene oxide) Macromonomers, Macromolecular Reports A32, 593-601 (1995).
Ober, Christopher K. and Kar P. Lok, Formation of large monodisperse copolymer particles by dispersion polymerization, Macromolecules, 20, 268-273 (1987).
Odian, George, Principles of Polymerization Second ed.; Wiley-Interscience: New York, U.S.A., pp. 194-204; 216-219; 271-275 (1981).
Ofir R, Seidman R, Rabinski T, Krup M, Yavelsky V, Weinstein Y and Wolfson M, Taxol-induced apoptosis un human SKOV3 ovarian and MCF7 breast carcinoma cells is caspase-3 and caspase-9 independent, Cell Death and Differentiation, 9, 636-642 (2002).
Pakunlu, R. 1., Wang, Y., Tsao, William, Pozharov, V., Cook, T. J., Minko, T., Enhancement of the Efficay of Chemotherapy for Lung Cancer by Simultaneous Suppression of Multidrug Resistance and Antiapoptotic Cellular Defense: Novel Multicomponent Delivery System, Cancer Research, 64, 6214-6224 (2004).
Pan, Jun et al., Development of a new poly(ethylene glycol)-graft-poly(D,L-lactic acid) as potential drug carriers, Journal of Biomedical Materials Research Part A, Apr. 2008, 89(1), 160-167.
PCT Search Report and Written Opinion: PCT/US2011/061902, mailed Jul. 30, 2012, which corresponds to U.S. Appl. No. 12/952,843 (9 pages).
PCT Search Report and Written Opinion: PCT/US2011/061917, mailed Jul. 20, 2012, which corresponds to U.S. Appl. No. 12/952,856 (10 pages).
Pridgen, Eric M., Robert Langer, Omid C Farokhzad Biodegradable, polymeric nanoparticle delivery systems for cancer therapy, Nanomedicine, 2(5), 669-80 (Oct. 2007).
Ramtoola, Z., Corrigan, O. I, Barrett, C. J., Release Kinetics of Fluphenazine from Biodegradable Microspheres, Journal of Microencapsulation, 9, 415-23 (1992).
Ranade, Vasant V., Drug delivery systems: 3B. Role of Polymers in Drug Delivery, The Journal of Clinical Pharmacology, 30, 107-120 (1990).
Ray, Biswajit and Broja M. Mandai, Dispersion polymerization of Acrylamide: Part II. 2,2"-Azobisisobutyronitrile initiator, Journal of Polymer Science: Part A: Polymer Chemistry, 37, 493-499 (1999).
Robinson, D. N., Peppas, N. A., Preparation and Characterization of pH-Responsive Poly(methacrylic acid-g-ethylene glycol) nanospheres, Macromolecules 35, 3668-74 (2002).
Rosler, A., Vandermeulen, W. M., Klok, H.-A., Advanced Drug Delivery Devices Via Self-Assembly of Amphiphilic Block Copolymers, Advanced Drug Delivery Reviews 53, 95-108 (2001).
Ryner, Maria, Anna Finne, Ann-Christine Albertsson, Hans R. Kricheldorf, L-lactide Macromonomer Synthesis Initiated by New Cyclic Tin Alkoxides Functionalized for Brushlike Structures, Macromolecules, 34, 7281-7287 (2001).
Sahoo, Sanjeeb K. and Labhasetwar Vinod, Enhanced Antiproliferative Activity of Transferrin-Conjugated Paclitaxel-Loaded Nanoparticles is Mediated via Sustained Intracellular Drug Retention, Molecular Pharmaceutics, 2(5), 373-383 (2005).
Sairam, Malladi, V. Ramesh Babu, Boya Vijaya Kumar Naidu, Tejraj M. Aminabhavi, Encapsulation efficiency and controlled release characteristics of crosslinked polyacrylamide particles, International Journal of Pharmaceutics, 320, 131-136 (2006).
Sant, S et al., Effect of polymer architecture on surface properties, plasma protein adsorption, and cellular interactions of pegylated nanoparticles, Journal Biomedical Materials Research Part 87A(4): 885-895 (2008).
Sarac, A. S., Redox Polymerization, Progress in Polymer Science, 24, 1149-1204 (1999).
Sawhney, Amarpreet S., Chandrashekhar P. Pathak and Jeffrey A. Hubbell, Bioerodible hydrogels based on photopolymerized poly(ethyleneglycol)-co-poly(.alpha.-hydroxy acid) diacrylate macromers, Macromolecules, 26:581-587 (1993).
Scheler, S et al., Cellular uptake and degradation behavior of biodegradable poly( ethylene glycol-graft-methyl methacrylate) nanoparticles crosslinked with dimethacryloyl hydroxylamine, International Journal Pharmaceutical 103, D207-218 (2011) (available online Oct. 2010).
Shenoy, D. B., Amiji, M. M., Poly( ethylene oxide)-modified poly(-caprolactone) Nanoparticles for Targeted Delivery of Tamoxifen in Breast Cancer, Int. J. Pharm., 293, 261-70 (2005).
Song, Jing-She, Frederic Trone, Mitchell A. Winnik, Monodisperse, controlled micron-size dye-labeled polystyrene particles by two stage dispersion polymerization, Polymer, 47, 817-825 (2005).
Soppimath, Kumaresh S., Tejraj M. Aminabhavi, Anandrao R. Kulkarni, Walter E. Rudzinski, Biodegradable polymeric nanoparticles as drug delivery devices, Journal of Controlled Release, 70, 1-20 (2001).
Torchilin, Vladimir, Multifunctional Nanocarriers, Advanced Drug Delivery Reviews, 58, 1532-1555 (2006).
Trail, P. A., Wilner, D., Lasch, S. J., Henderson, A. J., Hofstead, H., Casazza, A. M., Firestone, R. A., Hellstrom, K. E., Cure of Xenografted Human Carcinomas by BR96-Doxorubicin Immunoconjugates, Science 261, 212-15 (1993).
Ulbrich, K., V. Subr, L. W. Seymour, R. Duncan, Novel biodegradable hydrogels prepared using the divinylic crosslinking agent N,O-dimethacryloylhydroxylamine: 1. Synthesis and characterization of rates of gel degradation and rate of release of model drugs, in vitro and in vivo, Journal of Controlled Release, 24, 181-90 (1993).
Ulbrich, K., V. Subr, P. Podperova, M. Buresova, Synthesis of novel hydrolytically degradable hydrogels for controlled drug release, Journal of Controlled Release, 34, 155-65 (1995).
Vazquez, Blanca, Belen Levenfeld, Julio San Roman, Role of amine activators on the curing parameters, properties and tocixity of acrylic bone cements, Polymer International, 46, 241-50 (1998).
Wood, David A., Biodegradable drug delivery systems, International Journal of Pharmaceutics, 7, 1-18 (1980).
Xu, Peisheng, Edward A. Van Kirk, Shiyan Li, William J. Murdoch, Jun Ren, Muhammad Delwar Hussain, Maciej Radosz, Youquing Shen, Highly stable core-surface-crosslinked nanoparticles as cisplatin carriers for cancer chemotherapy, Colloids and Surfaces B: Biointerfaces, 48, 50-57 (2006).

(56) References Cited

OTHER PUBLICATIONS

Yang Tao, Fu-De Cui, Min-Koo Choi, Hongxia Lin, Suk-Jae Chung, Chang-Koo Shim, Dae-Duk Kim, Liposome Formulation of Paclitaxel with Enhanced Solubility and Stability, Drug Delivery, 14(5), 301-08 (2007).

Yin, W. al., Design of naltrexone-loaded hydrolyzable crosslinked nanoparticles, International Journal Pharmaceutical, 244, 9-19 (2002).

Yokoyama, M., Okano, T., Targetable Drug Carriers: Present Status and a Future Perspective, Advanced Drug Delivery Reviews 21, 77-80 (1996).

Zhao, Yue, Jie Fu, Dennis K. P. Ng, Chi Wu, Formation and Degradation of Poly(D,L-lactide) Nanoparticles and Their Potential Application as Controllable Releasing Devices, Macromolecular Bioscience, 4, 901-06 (2004).

* cited by examiner

Figure 4 (IR spectrum of paclitaxel-loaded hydrolyzable PEG-MMA (PDL)a nanospheres: fabricated with AIBN as an initiator)

Figure 5 (IR spectrum of paclitaxel-loaded hydrolyzable PEG-MMA (PDL)r nanospheres: fabricated with redox initiator system).

Figure 6 (IR spectrum of blank hydrolyzable PEG-MMA (8:4)a nanospheres fabricated with AIBN as the initiator)

Figure 7 (IR spectrum of blank hydrolyzable PEG-MMA (8:4)r nanospheres: fabricated with redox initiator system).

Figure 8 (IR spectrum of paclitaxel)

Figure 9 (IR spectrum of zapp88-loaded hydrolyzable PEG-MMA (ZDL)r nanospheres: fabricated with redox initiator system)

Figure 10 (IR spectrum of 2-chloro-3-diacetylamino-1,4-naphthoquinone (zapp88).)

Figure 11 (IR spectrum of zapp88-loaded hydrolyzable PEG-MMA (ZDL)a nanospheres: fabricated with AIBN as the initiator)

Figure 12 (Size distribution diagram for PEG-MMA (6:3)a nanospheres: fabricated with AIBN as the initiator at 6:3 ratio of for PEG:MMA)

Figure 13 (Size distribution diagram for PEG-MMA (10:4)a nanospheres: fabricated with AIBN as the initiator at 10:4 ratio of for PEG:MMA)

Figure 14 (Size distribution diagram for PEG-MMA (8:4)r nanospheres: fabricated with redox initiator system at 8:4 ratio of for PEG:MMA)

Figure 15 (Size distribution diagram for PEG-MMA (8:5)r nanospheres: fabricated with redox initiator system at 8:5 ratio of for PEG:MMA)

STEALTH POLYMERIC PARTICLES FOR DELIVERY OF BIOACTIVE OR DIAGNOSTIC AGENTS

CROSS-REFERENCE TO RELATED APPLICATION

This application is a divisional of U.S. application Ser. No. 12/952,856, filed Nov. 23, 2010, which is hereby incorporated herein by reference in its entirety.

STATEMENT REGARDING FEDERALLY SPONSORED RESEARCH OR DEVELOPMENT

This invention was made with government support under NIH Research Grant NIH CA138179 awarded by the Federal Agency "National Institutes of Health." The government has certain rights in the invention.

TECHNICAL FIELD

The present invention relates to the production and use of polymeric particles, which may be used to deliver therapeutic agents, imaging agents, and/or attached to ligands for site-specific targeting, wherein the polymer particles comprise polymeric particles (crosslinked or not crosslinked), which may be hydrolysable or not.

BACKGROUND OF THE INVENTION

One of the great challenges in medicine is finding more effective forms of treatment for a large number of life-threatening, but curable diseases, such as cancer. One of the challenges to be overcome relates to the inadequacies surrounding the ability to administer therapeutic agents, imaging agents, and ligands for site-specific targeting such that they selectively reach the desired targets without damaging healthy cells and/or without being blocked by biological barriers. Thus, to increase efficiency per dose of a therapeutic agent, efforts need to be made in the direction of increasing therapeutic agent and imaging agents' delivery, including circumventing the biological barriers that prevent therapeutic agent and imaging agents from reaching their targets.

Of particular interest is the development of delivery systems based on nanotechnology that can achieve both targeting (spatial/distribution control) and controlled release (temporal control) of drugs or therapeutic agents and imaging agents. This is because it is believed that if spatial targeting is combined with temporal controlled release, then an improved therapeutic index may be obtained. For example, if drug release or activation is made locally at the therapeutic site or biophase of interest, then selectivity will be increased by a multiplication of the spatial selectivity with the advantage of local drug release/activation. Further, the therapeutic index may be improved by a combination of spatially selected delivery and a preferable pattern of release for the therapeutic agent over long time periods or using a pulsatile release, which would be preferable for certain pharmacological activities of the therapeutic agents used in, for example, chronotherapeutics. See FIG. 1 for a schematic depiction of the combination of spatial and temporal forms of controlled delivery to achieve a double targeting of drug or therapeutic agent delivery.

Yokoyama et al (Advanced Drug Delivery Reviews, 1996, 21, 77-80) disclose a spatially directed delivery that is achieved with such a carrier system, and has a drug release that is only at a therapeutic site by local heating or cooling. Additionally, Thomas et al (Journal of Controlled Release, 1997, 48, 157-164) disclose a double targeting system that is a thermo-responsive polymeric micelle system. Also, Trail et al (Science 1993, 261, 212-215) disclose selective targeting to tumors and thermo-responsiveness using a polymeric micelle system by introduction of a thermo-responsive polymer segment.

SUMMARY OF THE INVENTION

The present invention relates to crosslinked or non-crosslinked polymeric particles (nanospheres), capable of double targeting, wherein the surface of the particle includes hydrophilic, neutral molecules that avoid recognition by biological barriers and a core that is crosslinked or not crosslinked to provide temporal controlled release of a therapeutic agent. Thus, a therapeutic or imaging agent may be more effectively delivered to a target while minimizing adverse side effects.

More specifically, the present invention relates to:

A polymer particle comprising a crosslinked or non-crosslinked polymer particle, wherein the crosslinked polymer polymeric particle comprises a copolymer of poly(alkene glycol-graft-methacrylate) that is crosslinked by at least one hydrolysable crosslinker.

The hydrolysable crosslinker may be N,O-dimethacryloyl hydroxylamine Examples of other types of crosslinker that can be used include, but are not limited to di(2-acryloyloxy ethoxy)-[4-hydroxyphenyl]methane, ethylene glycol dimethacrylate, 4,4'-di(methacryloylamino)azobenzene, N,N'-methylenebisacrylamide, tetraethylene glycol dimethacrylate, ethylene glycol divinyl carbonate, and methacryloxyethyl vinyl carbonate.

A polymer particle wherein the copolymer is poly(ethylene glycol-graft-methyl methacrylate).

A polymer particle core wherein the hydrolysable group is N,O-dimethacryloylhydroxylamine.

A polymer particle wherein a ratio of poly alkene glycol to acrylate is from about 12:1 to about 6:4.

A polymer particle wherein the amount of hydrolysable group is from about 0 mol % (for non-crosslinked particle) to about 4 mol % based on the total amount of copolymer.

A polymer particle wherein the average size is from about 50 nm to about 431.6 nm A polymer particle having a polydispersity of from about 0.0103 to about 0.507.

A polymer particle which further comprises a therapeutic agent.

A polymer particle which further comprises a therapeutic agent selected from the group consisting of 2-chloro-3-diacetylamino-1,4-naphthoquinone, docitaxel, doxorubicin, and paclitaxel.

In another embodiment, the present invention is related to a polymer particle comprising:

a crosslinked particle that is a product of starting materials comprising:
 (a) a hydrophilic monomer,
 (b) a hydrophobic monomer, and
 (c) a hydrolysable crosslinking agent.

A polymer particle wherein the hydrophilic monomer is an alkene glycol.

A polymer particle wherein the hydrophilic monomer is a poly(ethylene glycol) monomethyl ether mono methacrylate.

A polymer particle wherein the hydrophobic monomer is an acrylate.

A polymer particle wherein the hydrophobic monomer is methyl methacrylate.

A polymer particle wherein the hydrolysable crosslinking agent is N,O-dimethylacryloylhydroxylamine.

A polymer particle wherein a ratio of the hydrophilic monomer to the hydrophobic monomer is from about 12:1 to about 6:4.

A polymer particle wherein the amount of hydrolysable group is from about 0 mol % (for non-crosslinked particle) to about 4 mol % based on the total amount of the hydrophilic monomer and the hydrophobic monomer.

A polymer particle wherein the average size is from about 50 nm to about 431.6 nm.

A polymer particle wherein the polymer particle has a polydispersity of from about 0.0103 to about 0.507.

A polymer wherein the particle further comprises a therapeutic agent.

A polymer particle wherein the particle further comprises a therapeutic agent selected from the group consisting of 2-chloro-3-diacetylamino-1,4-naphthoquinone, docitaxel, doxorubicin, and paclitaxel.

In another embodiment, the present invention is a polymer particle comprising:

a crosslinked copolymer which comprises the following structures represented by Formulas (I), (II), and (III):

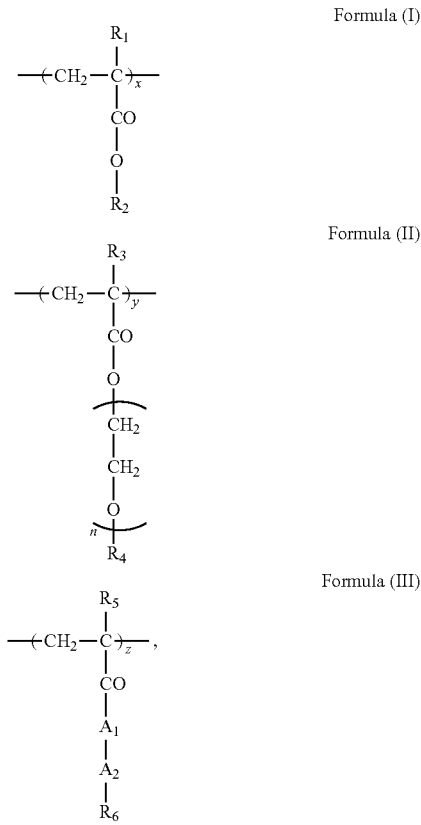

Formula (I)

Formula (II)

Formula (III)

wherein $R_1$-$R_5$ each represents a group, which may be the same or different from each other, and the group is selected from the group consisting of a hydrogen, a halogen, and an alkyl group having one to five carbon atoms, wherein $R_6$ represents another chain of the crosslinked polymer particle comprised of structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine. Formula III is not present in the non-crosslinked particles.

A polymer particle wherein $R_1$-$R_5$ each represents a methyl group.

A polymer particle comprising a noncrosslinked polymer particle which comprises structures represented by Formula (I) and (II) above.

A polymer particle wherein a ratio of the structure represented by Formula (I) to Formula (II) is from about 12:1 to about 6:4.

A polymer particle wherein the amount of Formula (I) relative to the amount of sum of Formulas (I) and (II) is from about 1 mol % to about 4 mol % based on the total amount of copolymer.

A polymer particle wherein the average size of the polymer particle is from about to 50 nm to about 431.6 nm.

A polymer particle wherein the polymer particle has a polydispersity of from about 0.0103 to about 0.507.

A polymer particle wherein the particle further comprises a therapeutic agent.

A polymer particle wherein the particle further comprises a therapeutic agent selected from the group consisting of 2-chloro-3-diacetylamino-1,4-naphthoquinone, docetaxel, doxorubicin and paclitaxel.

Another embodiment of the present invention is a method of preparing a hydrolysable crosslinker comprising the steps of (i) reacting an inhibitor with a polymerizable agent in a basic medium;

(ii) maintaining the reaction temperature below 30° C.;

(iii) letting the reaction mixture rest at room temperature for 10 hours; and (iv) neutralizing the reaction mixture.

A method of preparing a hydrolysable crosslinker wherein the basic medium is pyridine.

A method of preparing a hydrolysable crosslinker wherein the polymerizable agent is methacrylol chloride.

A method of preparing a hydrolysable crosslinker wherein the reaction mixture is neutralized in an organic medium.

A method of preparing a hydrolysable crosslinker wherein the organic medium is chloroform.

A method of preparing a hydrolysable crosslinker wherein the inhibitor is selected from the group consisting of edrophonium chloride, N-methylphysostigmine, neostigmine bromide, physostigmine sulfate, tacrine HCl, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-initrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzyl hydrazine HCl, hydralazine HCl, clorgyline HCl, L(−)-deprenyl HCl, D(+)-deprenyl HCl, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-a-methylbenzylamine PCMB), 8,9-dichloro-2,3,4,5-tetrahydro-1H-2-benzazepine hydrochloride, p-aminoglutethimide, (R+)-p-amino glutethimide tartrate, (S−)-p-aminoglutethimide tartrate, 3-iodotyrosine, (L−)-alpha-methyltyrosine, (D+)(L−)-alpha-methyltyrosine, acetazolamide, dichlorphenamide, 6-hydroxy-2-benzothiazolesulfonamide, and allopurinol.

In another embodiment, the present invention is a method of preparing polymer particles comprising the steps of (i) dissolving an acrylate, a poly(alkene glycol-graft-acrylate), a hydrolysable crosslinking agent, and an initiator in a solvent system;

(ii) stirring the reaction mixture in an oxygen free atmosphere;

(iii) leaving the reaction mixture to polymerize overnight in an oxygen free atmosphere; and, (iv) dialyzing in water.

A method of preparing polymer particles wherein the binary solvent system is ethanol and water.

A method of preparing polymer particles wherein the acrylate is methyl methacrylate.

A method of preparing polymer particles wherein the poly (alkeneglycol-graft-acrylate) is poly(ethyleneglycol-graft-methylmethacrylate).

A method of preparing polymer particles wherein the amount of methyl methacrylate (MMA) used is from 6.0 to 12.0 mmol.

A method of preparing polymer particles wherein the amount of MMA is 6.0 to 12.0 mmol, the amount of the hydrolysable crosslinking agent is from 1-4 mmol %, and the amount of initiator is 1 mol %.

A method of preparing polymer particles wherein the initiator is selected from the group consisting of benzoyl peroxide (BPO), azo-bis-isobutyronitrile (AIBN), N-Phenyl di ethanol amine (NPDEA), potassium persulfate (KPS), 2,2'-azobis-2,4-dimethylvaleronitrile (ADVN), PDMS macroazoinitiator (PDMS-azo), ammonium persulfate, thermal 2,2'-azobis[N-(2-carboxyethyl)-2-2-methylpropionamidine] (VA-057) (amphoteric pH sensitive initiator), BPO activated by tertiary amines such as: N,N-dimethyl-4-toluidine (DMT), N,N-dimethylbenzyl methacrylate, N,N-dimethylbenzyl alcohol, N,N-dimethylaniline, 4-N,N-dialkyl aminophenalkanoic acids and their methyl esters, peroxides, persulfate, peroxomonosulfate, peroxidiphosphate, metal ion oxidant-reducing agent systems which include but are not limited to Mn(III) and Mn(VII), Ce(IV), V(V), Co(III), Cr(VI) and Fe(II and III), 2,2-dimethoxy-2-phenylacetophenone, Quantacure ITX photosensitizer and Irgacure 907 (1-907) initiator systems, N-Phenyl diethanolamine, and N,N-dimethyl ethanol amine.

A method of preparing polymer particles wherein the initiator is a combination of BP and N, Phenyl Ditheanol Amine (NPDEA), used in a ratio of 50:50.

A method of preparing polymer particles wherein the amount of PEG-MA used is 0.1 mmol.

A method of preparing polymer particles wherein the amount of hydrolysable crosslinking agent used is from 1-4 mol % of the total volume of the reactants.

A method of preparing polymer particles wherein the hydrolysable crosslinking agent is N,O-dimethylacryloylhydroxylamine.

A method of preparing polymer particles wherein the initiator is azibisisobutyronitrile.

A method of preparing polymer particles wherein the amount of azibisisobutyronitrile is 1% of the total volume of the reactants.

A method of preparing polymer particles wherein the reaction mixture is heated to a temperature of 0° C.-60° C.

A method of preparing polymer particles further comprising a therapeutic agent in the reaction mixture.

A method of preparing polymer particles wherein the therapeutic agent is selected from the group consisting of 2-chloro-3-diacetylamino-1,4-naphthoquinone, docetaxel, doxorubicin, and paclitaxel.

A method of preparing polymer particles wherein the drug is paclitaxel.

The present disclosure relates to a polymer particle and methods of production and use thereof. The polymer particle may include a group capable of avoiding biological recognition (biofouling) and a group capable of being cleaved into two or more separate groups. The polymer particle may also contain a therapeutic agent.

The group capable of avoiding biological recognition is not particularly limited, so long as the group has the function of preventing proteins and biological molecules from binding to the surface of the polymer particle. The group capable of avoiding biological recognition may be a group that is hydrophilic and has a neutral charge, such as a polymer or an oligomer containing ether linkages (e.g., a polyether).

Examples of a group capable of avoiding biological recognition may include homo polymers or copolymers of polyalkene glycols, such as poly(ethylene glycol), poly(propylene glycol), poly(butylene glycol), and may included acrylates and acrylamide, such as hydroxyethyl methacrylate and hydroxypropylmethacrylamide respectively.

The group capable of being cleaved into two or more groups is not particularly limited, so long as the group is capable of being cleaved by the presence of specific environmental conditions. Examples of a group capable of being cleaved includes hydrolysable groups, biodegradable groups, heat and photo degradable groups.

A hydrolysable group may include a group that is capable of being cleaved by exposure to specific pH conditions. Examples of a hydrolysable group may include N,O-dimethylacryloylhydroxylamine which may be produced from starting materials such as hydroxylamine. Further, the hydrolysable group may have two or more functional groups, such as unsaturated bonds, such that the hydrolysable group may be incorporated into a crosslinking agent. By incorporating the hydrolysable group into a crosslinking agent, the crosslinking agent having the hydrolysable group may be copolymerized with another monomer to produce a crosslinked copolymer particle, wherein at least one of the crosslinking groups is hydrolysable under specific environmental conditions.

DETAILED DESCRIPTION OF THE INVENTION

Figure 1:
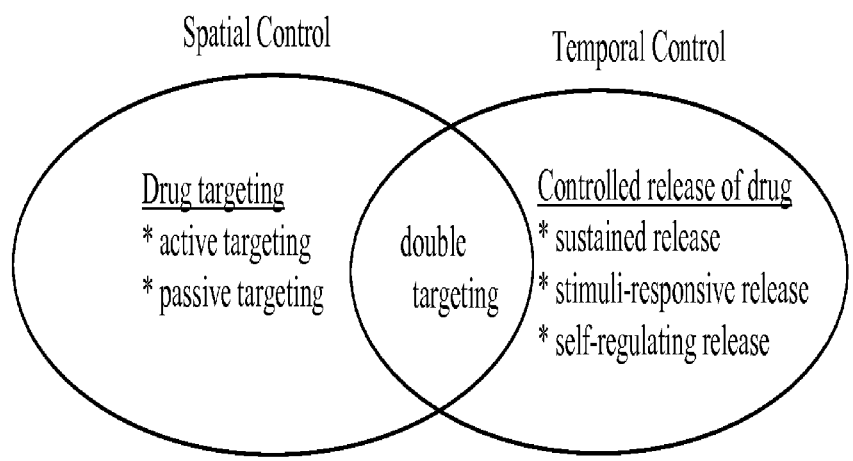
FIG. 1 is a prior art illustrative depiction of the combination of spatial and temporal forms of controlled delivery to achieve double targeting.
Figure 2:
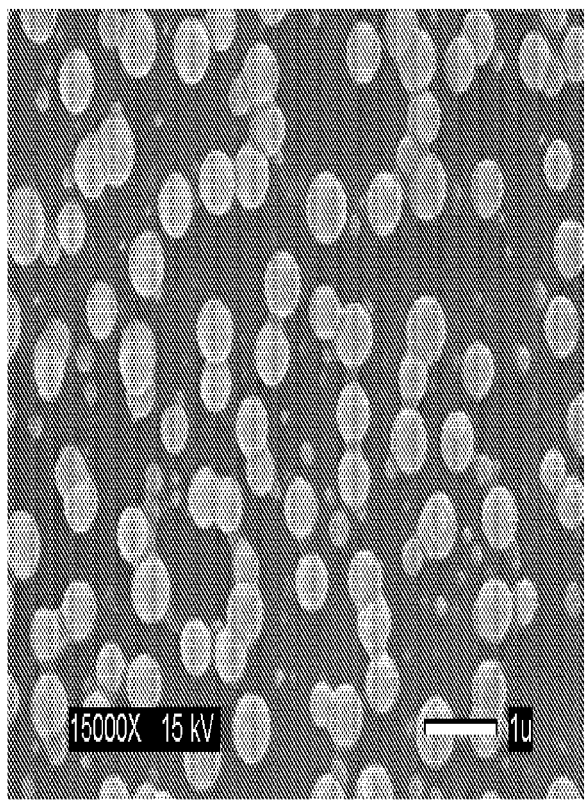
FIG. 2 is a scanning electron micrograph for polymethyl methacrylate (PMMA) (6:2)a nanospheres.
Figure 3:
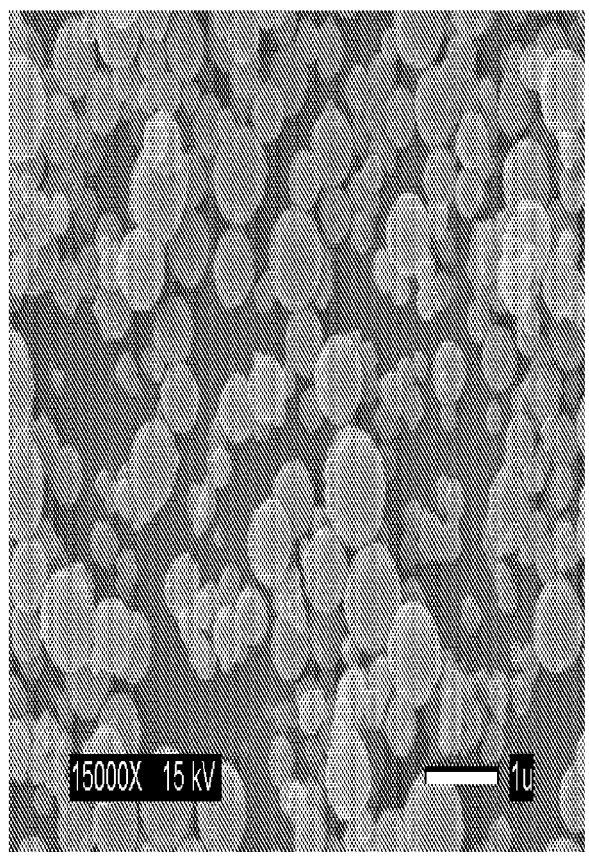
FIG. 3 is scanning electron micrograph for polyethylene glycol-methyl methacrylate (PEG-MMA) nanospheres.

In one embodiment, the polymer particles of the present invention include a crosslinked or non-crosslinked polymer particle, wherein the polymer particle comprises a copolymer of poly(alkene glycol-graft-acrylate) that is crosslinked or non-crosslinked by at least one hydrolysable monomer. For example, the copolymer may be a copolymer of at least one acrylate and may have an alkene glycol group attached as a pendant chain to form a brush or comb polymer. The copolymer may be a copolymer of poly(ethylene glycol-graft-methyl methacrylate), wherein the a ratio of alkene glycol to methylmethacrylate is preferably from about 12:1 to about 6:4. Further, the hydrolysable group may be N,O-dimethylacryloylhydroxylamine in the amount preferably of from about 1 mol % to about 4 mol % based on the total amount of the copolymer. The average size of the polymer particle may preferably be from about 50 nm to about 431.6 nm, and may have a polydispersity preferably of from about 0.0103 to about 0.507. The copolymer may include other macromonomers, which may or may not have functional groups.

Examples of the macromonomers may preferably include, but are not limited to, polyglycolide (PGA) macromonomer, polylactide (PLA) macromonomer, polycaprolactone (PCL) macromonomer, poly(lactide-co-glycolide) (PLGA) macromonomer, poly(propylene fumarate) PFF, methacryloyl-terminated PMMA macromonomer, methacrylate-terminated/functionalized poly(dimethylsiloxane) macromonomer (PDMS-MA), methacryloylpolystyrene (MA-Pst) (i.e., styrene macromonomers with methacryloyl end group), (vinylbenzyl)polystyrene (VB-Pst) (i.e., styrene macromonomers with a vinylbenzyl end group), 2-oxyethylmethacrylate-terminated PLLA macromonomer (MC), vinylbenzyl-terminated polyisoprene (PI) macromonomers, poly(ethylene glycol)-co-poly(a-hydroxyacid) diacrylate macromere, oligocaprolactone vinyl ether macromonomer, PEG-b-PLA macromer, PEG-b-PLA-b-PEG macromer, poly(ethylene oxide) (PEO) block functionalized with styryl, methacryloyl, thiol, maleate, vinyl, p-vinylphenylalkyl reactive end groups, methacryloxypropyl- and vinyl-terminal polysiloxanes, ω-methacryloylpoly(E-caprolactone) (PCL) macromonomer, poly(glycolide) macromonomers, HEMA terminated oligo(L-lactide) or oligo(D-lactide) macromonomers, oligoNIPAAm and polyNIPAAm macromonomers, poly(n-butylacrylate) macromonomers, n-butyl acrylate, methyl acrylate (MA), methyl methacrylate (MMA), N,N'-dimethyl acrylamide (DMA); N-vinyl pyrrolidone (VP), hydroxyethyl methacrylate, n-butyl methacrylate, acrylamide, hydrophilic N-(2-hydroxypropylmethacrylamide) (HPMA), methyl-, ethyl-butyl-, octylcyanoacrylates (anionic polymerization) to form poly(alkyl cyan oacrylates)(PACA) (biodegradable, pH sensitive), acrylic acid, 2-hydroxypropyl methacrylate (HPMA), N,N-dimethylaminoethyl methacrylate (DMAEMA) and hydrophilic polymers or macromonomers.

Further examples of the macromonomers may preferably include, but are not limited to, poly(vinyl pyrrolidone), hydroxypropyl cellulose (HPC), poly(acrylic acid), poly[N-(2-hydroxypropyl) methacrylamide] (PHMPA), dextrans e.g., dextran-10, -40, -70, poloxamer-188, -184, -237, polyethylene glycol (PEG), polyethylene oxide (PEO) and PEO macromonomers with p-vinylbenzyl and methacrylate end groups, poloxamine, polysorbates, methacryloyl-terminated poly(ethylene oxide) macromonomer, poly(2-alkyl-2-oxazolin), poly(methacrylic acid), poly(acrylic acid) macromonomers, bifunctional vinyl urethane macromonomers, vinyl terminus polysiloxane macromonomer, poly(vinyl alcohol), polyacrylamide, and poly(glutaraldehyde).

The acrylate in the copolymer is not particularly limited, and may be any acrylate or acrylamide. Examples of the acrylates and acrylamides include, but are not limited to, n-butyl acrylate, methyl acrylate (MA), methyl methacrylate, N,N'-dimethyl acrylamide (DMA), N-vinyl pyrrolidone (VP), hydroxyethyl methacrylate, acrylamide, N-(2-hydroxypropylmethacrylamide) (HPMA), methyl-, ethyl-butyl-, octylcyanoacrylates, acrylic acid, and N,N-dimethylaminoethyl methacrylate (DMAEMA).

In another embodiment, the particle polymer includes a crosslinked polymer particle that is a product of starting materials including: (a) a hydrophilic monomer, (b) a hydrophobic monomer, and (c) a hydrolysable crosslinking agent.

The hydrophilic monomer may preferably include an alkene glycol, such as a poly(ethylene glycol) monomethyl ether mono methacrylate. The hydrophobic monomer may preferably include an acrylate, such as methyl methacrylate. The crosslinked polymer particle may be produced from the polymerization of starting materials, including a hydrophilic monomer and a hydrophobic monomer, wherein a ratio of the hydrophilic monomer to the hydrophobic monomer is preferably from about 12:1 to about 6:4. The crosslinked copolymer may include a hydrolysable crosslinking agent is N,O-dimethylacryloylhydroxylamine in an amount preferably from about 1 mol % to about 4 mol % based on the total amount of the hydrophilic monomer and the hydrophobic monomer. The average size of the polymer particle may preferably be from about 50 nm to about 431.6 nm, with a polydispersity preferably of from about 0.0103 to about 0.507. The copolymer may include other monomers or macromonomers, which may or may not have functional groups. The acrylate in the copolymer is not particularly limited, and may be any acrylate.

Examples of the macromonomers may preferably include, but are not limited to, polyglycolide (PGA), polylactide (PLA), polycaprolactone (PCL), poly(lactide-co-glycolide) (PLGA), poly(propylene fumarate) PFF, methacryloyl-terminated PMMA macromonomer, methacrylate-terminated/functionalized poly(dimethylsiloxane) macromonomer (PDMS-MA), methacryloylpolystyrene (MA-Pst) (i.e., styrene macromonomers with methacryloyl end group), (vinylbenzyl)polystyrene (VB-Pst) (i.e., styrene macromonomers with a vinylbenzyl end group), 2-oxyethylmethacrylate-terminated PLLA macromonomer (MC), vinylbenzyl-terminated polyisoprene (PI) macromonomers, poly(ethylene glycol)-co-poly(α-hydroxyacid) diacrylate macromers, oligocaprolactone vinyl ether macromonomer, PEG-b-PLA macromer, PEG-b-PLA-b-PEG macromer, poly(ethylene oxide) (PEO) block functionalized with styryl, methacryloyl, thiol, maleate, vinyl, p-vinylphenylalkyl reactive end groups, methacryloxypropyl- and vinyl-terminal polysiloxanes (Kim et al., 2005), ω-methacryloylpoly(E-caprolactone) (PCL) macromonomer, poly(glycolide) macromonomers, HEMA terminated oligo(L-lactide) or oligo(D-lactide) macromonomers, oligoNIPAAm and polyNIPAAm macromonomers, poly(n-butylacrylate) macromonomers, n-butyl acrylate, methyl acrylate (MA), methyl methacrylate (MMA), N,N'-dimethyl acrylamide (DMA); N-vinyl pyrrolidone (VP), hydroxyethyl methacrylate, n-butyl methacrylate, acrylamide, hydrophilic N-(2-hydroxypropylmethacrylamide) (HPMA), methyl-, ethyl-butyl-, octylcyanoacrylates (anionic polymerization) to form poly(alkylcyanoacrylates) (PACA) (biodegradable, pH sensitive), acrylic acid, 2-hydroxypropyl methacrylate (HPMA), N,N-dimethylaminoethyl methacrylate (DMAEMA) and hydrophilic polymers or macromonomers.

Examples of the macromonomers may preferably include, but are not limited to, poly(vinyl pyrrolidone), hydroxypropyl cellulose (HPC), poly(acrylic acid), poly[N-(2-hydroxypropyl) methacrylamide] (PHMPA), dextrans eg dextran-10, -40, -70, poloxamer-188, -184, -237, polyethylene glycol (PEG), polyethylene oxide (PEO) and PEO macromonomers with p-vinylbenzyl and methacrylate end groups, poloxamine, polysorbates, methacryloyl-terminated poly(ethylene oxide) macromonomer, poly(2-alkyl-2-oxazolin), poly(methacrylic acid), poly(acrylic acid) macromonomers, bifunctional vinyl urethane macromonomers, vinyl terminus polysiloxane macromonomer, poly(vinyl alcohol), polyacrylamide, and poly(glutaraldehyde). Poly(isobutylene), poly(12-hydroxystearic acid), poly (2-ethylhexyl methacrylate) have also been employed as stabilizers in hydrocarbon solvents.

In one embodiment, the polymer particle includes a crosslinked copolymer comprising structures represented by the Formulae (I), (II), and (III):

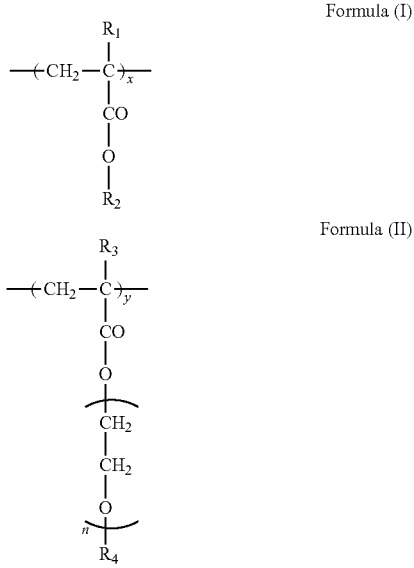

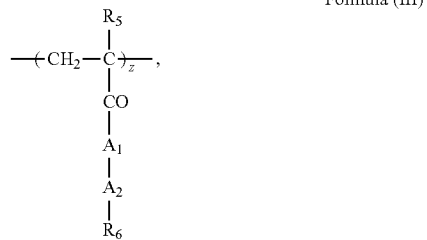

wherein $R_1$-$R_5$ each represents a group, which may be the same or different from each other, and the group is selected from the group consisting of a hydrogen, a halogen, and an alkyl group having one to five carbon atoms; $R_6$ represents another chain of the crosslinked polymer particle comprised of structures represented by Formulae (I), (II), and (III); x, y, and z represent an integer from 1 to 100; n represents an integer 1 to 10,000; $A_1$ is an oxygen atom or a secondary amine; and $A_z$ is an oxygen atom or a secondary amine. The polymer particle may include a structure, wherein $R_1$-$R_5$ each represent a methyl group, the ratio of the structure represented by Formula (I) to Formula (II) is from about 12:1 to about 6:4, the amount of Formula (I) relative to the amount of sum of Formulas (I) and (II) is preferably from about 1 mol % to about 4 mol % based on the total amount of copolymer, and the average size of the polymer particle is preferably from about to 95.9 nm to about 431.6 nm, and preferably has a polydispersity from about 0.0103 to about 0.507.

Examples of crosslinkers used in the preparation of the polymer particles described above include, but are not limited to, poly(propylene fumarate)-diacrylate (PFF-DA) macromer, N-vinyl pyrrolidone—to form PVP crosslinks, poly(ethylene glycol)-dimethacrylate (PEG-DMA), ethylene glycol dimethacrylate (EGDMA), 4,4'-di(methacryloylamino) azobenzene (DMAAB), N,N'-methylenebisacrylamide, hydrophilic N-isopropyl acrylamide, divinyl benzene (DVB), tetraethylene glycol dimethacrylate, ethylene glycol divinyl carbonate (EGDVC); and, methacryloxyethyl vinyl carbonate (HEMAVC).

Examples of solvents used in the preparation of the polymer particles described above include, but are not limited to, dichloromethane, water, ethanol, hexane, ethyl acetate, chloroform, acetone, tetrahydrofuran, dimethylsulfoxide (DMSO) and the like.

Examples of initiators used in the preparation of the polymer particles described above include, but are not limited to, benzoyl peroxide (BPO), azo-bis-isobutyronitrile (AIBN), potassium persulfate (KPS), 2,2'-azobis-2,4-dimethylvaleronitrile (ADVN), PDMS macroazoinitiator (PDMS-azo), ammonium persulfate, thermal 2,2'-azobis[N-(2-carboxyethyl)-2-2-methylpropionamidine](VA-057) (amphoteric pH sensitive initiator), redox initiators, and photoinitiators.

Examples of redox initiators include, but are not limited to, BPO activated by tertiary amines such as: N,N-dimethyl-4-toluidine (DMT), N,N-dimethylbenzyl methacrylate, N,N-dimethylbenzyl alcohol, N,N-dimethylaniline, 4-N,N-dialkyl aminophenalkanoic acids and their methyl esters, peroxides, persulfate, N-Phenyldiethanolamine (NPDEA), peroxomonosulfate, peroxidiphosphate, metal ion oxidant-reducing agent systems which include but are not limited to Mn(III) and Mn(VII), Ce(IV), V(V), Co(III), Cr(VI) and Fe(II and III).

Examples of photoinitiators include, but are not limited to 2,2-dimethoxy-2-phenylacetophenone, Quantacure ITX photosensitizer and Irgacure 907 (1-907) initiator systems, and N,N-dimethyl ethanol amine.

Any of the above embodiments may also include a therapeutic agent, wherein the therapeutic agent is contained or encapsulated inside the polymer particle. The polymer particle may then function as a package for controlling the delivery of the therapeutic agent under predetermined environmental conditions. For example, in one embodiment, a therapeutic agent might be incorporated into the particle during the copolymerization process. The particle polymer would then prevent the therapeutic agent from prematurely being absorbed by the body or encountering biological barriers, such as macrophages, or even being prematurely excreted as waste. When the polymer particle is exposed to the predetermined environmental conditions, the group capable of being cleaved into two or more groups would be cleaved into two or more groups to reduce crosslinking in such a way as to release the therapeutic agent from the interior of the polymer particle to the local environment. The specific nature of the predetermined environmental conditions necessary to effect release would be determined by the choice of the group capable of being cleaved into two or more groups. For example, when the group capable of being cleaved into two or more groups is a hydrolysable group such as N,O-dimethylacryloylhydroxylamine or a polymer particle produced from N,O-dimethylacryloylhydroxylamine, then the therapeutic agent is stable at pH values below 5 and degraded at higher pH.

The term therapeutic agent includes pharmacologically active substances that produce a local or systemic effect in a mammal. The term thus means any substance intended for use in the diagnosis, cure, mitigation, treatment or prevention of a disease or in the enhancement of desirable physical or mental development and conditions in a mammal.

Therapeutic entities for employment with the responsive nanoparticles and for the formation of mixed polymer particles described herein therefore include small molecule compounds, polypeptides, proteins, and nucleic acids.

Examples of proteins preferably include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the analogues and congeners thereof.

Classes of therapeutic agents include pharmaceutically active compounds which can be loaded into a polymer particle include, but are not limited to, anti-AIDS agents, anti-cancer agents, antibiotics, immunosuppressants (e.g., cyclosporine) anti-viral agents, enzyme inhibitors, neurotoxins, opioids, hypnotics, antihistamines, tranquilizers, anti-convulsants, muscle relaxants and anti-Parkinson agents, anti-spasmodics and muscle contractants, miotics and anti-cholinergics, antiglaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic agents, anti-emetics, imaging agents, specific targeting agents, neurotransmitters, proteins, cell response modifiers, and vaccines.

A more complete listing of classes of compounds suitable for loading into polymers using the present methods may be found in the Pharmazeutische Wirkstoffe (Von Kleemann et al. (eds) Stuttgart/New York, 1987, incorporated herein by reference). Examples of particular pharmaceutically active substances are presented below.

Anti-AIDS agents are substances used to treat or prevent Autoimmune Deficiency Syndrome (AIDS). Examples of such agents include CD4, 3'-azido-3'-deoxythymidine (AZT), 9-(2-hydroxyethoxymethyl)-guanine acyclovir, phosphonoformic acid, 1-adamantanamine, peptide T, and 2',3' dideoxycytidine.

Anti-cancer agents are substances used to treat or prevent cancer. Examples of such agents include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: 5-(3,3)-dimethyl-1-triazenyl)imidazole-4-carboxamide), methotrexate, fluorouracil, 5-fluorouracil, cytarabine, cytosine arabinoxide, mercaptopurine, 6-mercaptopurine, and thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromicin and cephalosporins.

Anti-viral agents are substances capable of destroying or suppressing the replication of viruses. Examples of anti-viral agents include a-methyl-P-adamantane methylamine, 1-D-ribo furanosyl-1,2,4-triazole-3 carboxamide, 9-(2-hydroxy-ethoxymethylguanine), adamantanamine, 5-iodo-2'-deoxyuridine, trifluorothymidine, interferon, and adenine arabinoside.

Enzyme inhibitors are agents which inhibit an enzymatic reaction. Examples of enzyme inhibitors include edrophonium chloride, N-methylphysostigmine, neostigmine bromide, physostigmine sulfate, tacrine HCl, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-initrocatechol, diacylglyccrol kinasc inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, L(−)-deprenyl HCl, D(+)-deprenyl HCl, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-a-methylbenzylamine PCMB), 8,9-dichloro-2,3,4,5-tetrahydro-1H-2-benzazepine hydrochloride, p-aminoglutethimide, (R+)-p-aminoglutethimide tartrate, (S−)-p-aminoglutethimide tartrate, 3-iodotyrosine, (L−)-alpha-methyltyrosine, (D+)(L−)-alpha-methyltyrosine, acetazolamide, dichlorphenamide, 6-hydroxy-2-benzothiazolesulfonamide, and allopurinol.

Neurotoxins are agents which have a toxic effect on the nervous system, e.g., nerve cells. Some examples of neurotoxins include, but are not limited to, adrenergic neurotoxins, cholinergic neurotoxins, dopaminergic neurotoxins, and other neurotoxins. Examples of adrenergic neurotoxins include, but are not limited to, N-(2-chloroethyl)-N-ethyl-2-bromobenzylamine hydrochloride. Examples of cholinergic neurotoxins include, but are not limited to, acetylethylcholine mustard hydrochloride. Examples of dopaminergic neurotoxins include, but are not limited to, 6-hydroxydopamine HBr, 1-methyl-4-(2-methylphenyl)-1,2,3,6-tetrahydropyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide.

Opioids are agents having opiate like effects that are not derived from opium. Some examples of opioids include, but are not limited to, opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chloronaltrexamine hydrochloride funaltrexamine HCl, nalbuphine HCl, nalorphine HCl, naloxone HCl, naloxonazine, naltrexone HCl, and naltrindole HCl.

Hypnotics are agents which produce a hypnotic effect. Some examples of hypnotics include, but are not limited to, pentobarbital sodium, phenobarbital, secobarbital, thiopental and mixtures, thereof, heterocyclic hypnotics, dioxopiperidines, glutarimides, diethyl isovaleramide, α-bromoisovaleryl urea, urethanes and disulfanes.

Antihistamines are agents which competitively inhibit the effects of histamines. Some examples of antihistamines include, but are not limited to, pyrilamine, chlorpheniramine, tetrahydrazoline, and the like.

Lubricants are agents that increase the lubricity of the environment into which they are delivered. Some examples of biologically active lubricants include, but are not limited to, water and saline.

Tranquilizers are agents which provide a tranquilizing effect. Some examples of tranquilizers include, but are not limited to, chloropromazine, promazine, fluphenzaine, reserpine, deserpidine, and meprobamate.

Anti-convulsants are agents which have an effect of preventing, reducing, or eliminating convulsions. Some examples of such agents include, but are not limited to, primidone, phenytoin, valproate, and ethosuximide.

Muscle relaxants and anti-Parkinson agents are agents which relax muscles or reduce or eliminate symptoms associated with Parkinson's disease. Some examples of such agents include, but are not limited to, mephenesin, methocarbomal, cyclobenzaprine hydrochloride, trihexylphenidyl hydrochloride, levodopa/carbidopa, and biperiden.

Anti-spasmodics and muscle contractants are agents capable of preventing or relieving muscle spasms or contractions. Some examples of such agents include, but are not limited to, atropine, scopolamine, oxyphenonium, and papaverine.

Miotics and anti-cholinergics are agents which cause bronchodilation. Some examples of miotics and anti-cholinergics include, but are not limited to, echothiophate, pilocarpine, physostigmine salicylate, diisopropylfluorophosphate, epinephrine, neostigmine, carbachol, methacholine, bethanechol, and the like.

Anti-glaucoma agents include, but are not limited to, betaxalol, pilocarpine, timolol, timolol salts, and combinations of timolol, and/or its salts, with pilocarpine.

Anti-parasitic, -protozoal and -fungal agents include, but are not limited to, ivermectin, pyrimethamine, trisulfapyrimidine, clindamycin, amphotericin B, nystatin, flucytosine, natamycin, and miconazole.

Anti-hypertensives are agents capable of counteracting high blood pressure. Some examples of such substances include, but are not limited to, alpha-methyldopa and the pivaloyloxyethyl ester of alpha-methyldopa.

Analgesics are agents capable of preventing, reducing, or relieving pain. Some examples of analgesics include, but are not limited to, morphine sulfate, codeine sulfate, meperidine, and nalorphine.

Anti-pyretics are agents capable of relieving or reducing fever and anti-inflammatory agents are substances capable of counteracting or suppressing inflammation. Some examples of such agents include, but are not limited to, aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are agents which have an anesthetic effect in a localized region. Some examples of such anesthetics include, but are not limited to, procaine, lidocaine, tetracaine and dibucaine.

Ophthalmics include, but are not limited to, diagnostic agents such as sodium fluorescein, rose bengal, methacholine, adrenaline, cocaine, and atropine. Ophthalmic surgical additives include, but are not limited to, alpha-chymotrypsin and hyaluronidase.

Prostaglandins are art recognized and are a class of naturally occurring chemically related, long-chain hydroxy fatty acids that have a variety of biological effects. Some examples of prostaglandins include, but are not limited to prostandin (prostaglandin $E_1$), Dinoprost (prostaglandin $E_{2\alpha}$), and minprostin $E_2$ (prostaglandin $E_2$)

Anti-depressants are agents capable of preventing or relieving depression. Some examples of anti-depressants include, but are not limited to, imipramine, amitriptyline, nortriptyline, protriptyline, desipramine, amoxapine, doxepin, maprotiline, tranylcypromine, phenelzine and isocarboxazide.

Anti-psychotic substances are agents which modify psychotic behavior. Some examples of such agents include, but are not limited to, phenothiazines, butyrophenones and thioxanthenes.

Anti-emetics are agents which prevent or alleviate nausea or vomiting. An example of such a substance includes, but is not limited to, dramamine.

In topical skin care applications, a variety of active agents may be advantageously employed. By way of example only suitable active agents which may be incorporated into the cosmetic composition include anti-aging active substances, anti-wrinkle active substances, hydrating or moisturizing or slimming active substances, depigmenting active substances, substances active against free radicals, anti-irritation active substances, sun protective active substances, anti-acne active substances, firming-up active substances, exfoliating active substances, emollient active substances, and active substances for the treating of skin disorders such as dermatitis and the like.

Imaging agents are agents capable of imaging a desired site, e.g., tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g., a tumor, and providing a therapeutic effect. Examples of targeting agents include agents which can carry toxins or other agents which provide beneficial effects. The targeting agent can be an antibody linked to a toxin, e.g., ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

As those skilled in the art will appreciate, the foregoing therapeutic agents are exemplary only. Because the polymer particles of the present invention disclosed herein are suited for application under a variety of physiological conditions, a wide variety of therapeutic agents may be loaded into the polymer particles described herein and administered.

Scheme 1 shows the synthesis of the polymer particles (nanospheres) as embodied by hydrolyzable crosslinked PEG-PMMA nanospheres, wherein hydrolyzable crosslinked PEG-PMMA nanospheres (A=N,O-dimethacryloyl hydroxylamine (XL); B=methyl methacrylate (MMA); C=poly(ethylene glycol)n monomethyl ether monomethacrylate (PEG-MA; n=1000); D=the crosslinked polymer).

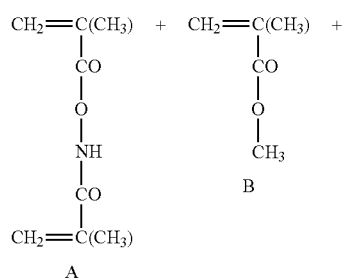

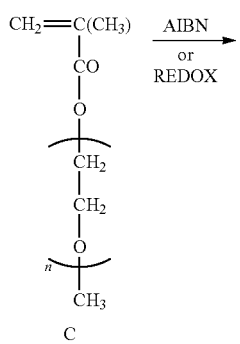

EXPERIMENTAL

Materials

Methacryol chloride (98%: obtained from Bimax Cor.) and methyl methacrylate (99%, Aldrich) were vacuum distilled prior to use. 2,2'-Azobisisobutyronitrile (AIBN) (98%, Aldrich) was recrystallized from methanol before use. Paclitaxel (95%, Aldrich), hydroxylamine hydrochloride (99%, Aldrich), pyridine (99%+, Aldrich), diethyl ether (99.8%, Aldrich), ethyl alcohol (denatured, Sigma-Aldrich), methyl alcohol (99.93%, Sigma-Aldrich), methyl sulfoxide (99.99%, Aldrich), acetonitrile (99.93+%, Sigma-Aldrich), 1-octanol (99+%, Sigma-Aldrich), and hydrochloric acid (37%, Fisher Scientific) were used as received. Poly(ethylene glycol)n monomethyl ether mono methacrylate (PEG-MA), (n=1000; Polysciences Inc.), benzoyl peroxide (BP) (97%, Aldrich) and N-phenyldiethanolamine (NPDEA) (97%, Aldrich) were used without further purification.

Example 1

Synthesis of Hydrolysable Crosslinker (N,O-Dimethylacryloyl Hydroxylamine)

The crosslinker, N,O-dimethacryloylhydroxylamine was synthesized as follows.

To a solution of hydroxylamine hydrochloride (9.0 g) in 72 ml of pyridine, methacrylol chloride (27 ml) was added dropwise with stirring. The temperature of the mixture was kept below 30° C. The reaction mixture was left at room temperature for 10 hours. It was dissolved in 150 ml chloroform and then neutralized with 48 ml HCl. The product was extracted with distilled water (4×150 ml), dried over magnesium sulfate and then dissolved in ether, followed by filtration, drying and recrystallization.

The resulting crosslinker, N,O-dimethacryloylhydroxylamine was characterized by $^1$H NMR analysis and melting point determination to confirm its identity and purity. The data obtained {m.p.: 55-56° C.; $^1$H NMR (400 MHz, CDCl$_3$): (C$_8$H$_{11}$NO$_3$) δ=2.04 (s, 3H), 2.08 (s, 3H) 5.54, 5,8 (s, 2H), 5.9, 6.38 (s, 2H), 9.25 (s, 1H)}.

Characterization of 2-chloro-3-diacetylamino-1,4-naphthoquinone (Zapp88)

2-chloro-3-diacetylamino-1,4-naphthoquinone (Zapp88) previously synthesized as in Bakare et al (*Bioorganic & Medicinal Chemistry* 2003, 11, 3165-3170, which is incorporated herein by reference). 2-chloro-3-diacetylamino-1,4-naphthoquinone was characterized by $^1$H NMR and IR analyses and melting point determination to confirm its identity and purity. The data obtained {m.p.: 161-163° C.; $^1$H NMR (400 MHz, CDCl$_3$): (C$_8$H$_{11}$NO$_3$) δ=2.35 (s, 6H), 7.23-7.29 (m, 2H), 8.16-8.28 (m, 2H); IR (cm$^{-1}$) 3447, 2932, 1742, 1706, 1675, 1608, 1592, 1421, 1367, 1320, 1224, 1126, 1068, 1041, 971, 874, 718, 629, 598}.

Example 2

Synthesis of Nanospheres

Two different initiator systems were used; (i) radical generation by thermal decomposition system ∎AIBN and (ii) the radical generation by redox system—BPO and NPDEA. The initiator concentration was kept constant at 1 mol % of the total polymerizable components (Table 3.1 and 3.2). The empty nanospheres are therefore referred to as PEG-PMMA (M:X)n, where M and X represent the mmole of MMA and XL the mol % of the crosslinker based on the concentration of MMA and PEG-MA respectively and n denotes the initiator system and is either be a (for AIBN) or r (for the redox system). These notations can be used in defining the resulting blank nanospheres. The drug-loaded nanospheres would be identified as PEG-PMMA (DDL)n where D represents the drug used and is either P denoting paclitaxel or Z denoting Zapp88. The notation n remains as previously defined representing the type of initiator system and would either be a (for AIBN) or r (for the redox initiators). The following sections describe the experiments that were carried out.

Non-crosslinked nanoparticles were produced using the same procedure except that the crosslinker was not used.

Example 3

Synthesis of Empty Hydrolyzable Crosslinked Poly(ethylene glycol-co-methyl methacrylate) {PEG-PMMA (M:X)a} Nanospheres A 4$^2$ factorial experiment replicated twice was designed and carried out by varying the crosslinker concentration (factor 1 at four levels) and the concentration of the methylmethacrylate (factor 2 at four levels) as shown in Table 1.1. For all the polymerization reactions, the amount of PEG-MA macromonomer was kept constant at 0.1 mmol and the initiator was held constant at 1% of the polymerizable components. The nanospheres were synthesized by the free radical dispersion polymerization technique. Into a round bottom flask equipped with a magnetic stirrer and containing a binary solvent system (ethanol:water in appropriate ratio (1 to 100 mL), MMA (6.0-12.0 mmol), PEG-MA (0.1 mmol), crosslinker (1-4 mol %)] and AIBN (1%) were added. The flask was sealed and nitrogen gas was bubbled through the mixture before the content was heated to 60° C. The polymerization was allowed to proceed overnight with continuous flow of nitrogen gas. On the completion of the reaction, the product was a translucent liquid. The obtained PEG-PMMA (M:X)a nanospheres were dialyzed in water, freeze-dried and stored in vials at 4° C. Table 3.1 summarizes the feed compositions for the PEG-PMMA (M:X)a nanospheres.

Example 4

Synthesis of Empty Hydrolyzable Crosslinked Poly(ethylene glycol-co-methyl methacrylate) {PEG-PMMA (M:X)r} Nanospheres The PEG-PMMA (M:X)r nanospheres were synthesized by selecting the PEG-PMMA (8:4)a formulation as a reference. The reaction conditions were however slightly modified. MMA concentration was kept constant at 8.0 mmol while XL concentration was varied between 4-5 mol % (Table 1.2). The initiator (redox) concentration was kept constant at 1 mol %. However, since the redox initiator system comprises two co-initiators, BP and NPDEA, the co-initiators were used in a 50:50 ratio.

Into a round bottom flask equipped with a magnetic stirrer and containing a binary solvent system [ethanol:water (50:50)] (10 mL), MMA (856 µL, 8.0 mmol), PEG-MA (100 mg, 0.1 mmol), XL [54.8-68.5 mg, 0.324-0.405 mmol (1-4 mmol %)] and co-initiators: BP and NPDEA [0.0842-0.0851 mmol (1 mol %)] were added. The flask was sealed and nitrogen gas was bubbled through the mixture. The polymerization was allowed to proceed overnight with continuous flow of nitrogen gas. On the completion of the reaction, the product was a translucent liquid. The obtained PEG-PMMA (8:X)r nanospheres were dialyzed in water for five days, freeze-dried and stored in vials at 4° C. Table 1.2 summarizes the different variations in MMA and XL feed compositions for the PEG-PMMA (8:X)r nanospheres.

Example 5

Synthesis of Drug-Loaded Hydrolyzable Crosslinked Poly(ethylene glycol co-methyl methacrylate) {PEG-PMMA (DDL)n} Nanospheres The drug-loading experiments were carried out using a fixed amount of the drug (10 mg). This weight of the drug is about 1.05 (w/w) of the combined weights of the total monomers (Table 1.3). The PEG-PMMA (8:4)n formulation was used under both initiator systems. The polymerization procedure was the same as previously described for the empty nanospheres except for the inclusion of the drug in the reaction mixture. The purification step was slightly modified. After the polymerization, the resulting product was centrifuged at 10,000 rpm to collect the solid particles. The supernatant was decanted and discarded while the pellet was dispersed in 2 mL filtered distilled water, freeze-dried and stored in vials at 4° C. Table 1.3 summarizes the feed compositions for the PEG-PMMA (DDL)n nanosphere.

TABLE 1.1

Variations in MMA and XL Compositions for the Preparation of Empty PEG-PMMA (M:X)a Nanospheres

| Sample Name | Amount of MMA | Amount of XL* |
|---|---|---|
| PEG-PMMA (6:1)a | 6.0 mmol | 1 mol % |
| PEG-PMMA (6:2)a | 6.0 mmol | 2 mol % |
| PEG-PMMA (6:3)a | 6.0 mmol | 3 mol % |
| PEG-PMMA (6:4)a | 6.0 mmol | 4 mol % |

TABLE 1.1-continued

Variations in MMA and XL Compositions for the Preparation
of Empty PEG-PMMA (M:X)a Nanospheres

| Sample Name | Amount of MMA | Amount of XL* |
|---|---|---|
| PEG-PMMA (8:1)a | 8.0 mmol | 1 mol % |
| PEG-PMMA (8:2)a | 8.0 mmol | 2 mol % |
| PEG-PMMA (8:3)a | 8.0 mmol | 3 mol % |
| PEG-PMMA (8:4)a | 8.0 mmol | 4 mol % |
| PEG-PMMA (10:1)a | 10.0 mmol | 1 mol % |
| PEG-PMMA (10:2)a | 10.0 mmol | 2 mol % |
| PEG-PMMA (10:3)a | 10.0 mmol | 3 mol % |
| PEG-PMMA (10:4)a | 10.0 mmol | 4 mol % |
| PEG-PMMA (12:1)a | 12.0 mmol | 1 mol % |
| PEG-PMMA (12:2)a | 12.0 mmol | 2 mol % |
| PEG-PMMA (12:3)a | 12.0 mmol | 3 mol % |
| PEG-PMMA (12:4)a | 12.0 mmol | 4 mol % |

Note:
*The combined concentrations of MMA and PEG-MA.

TABLE 1.2

Variations in XL Composition for the Preparation
of Empty PEG-PMMA (8:X)r Nanospheres

| Sample Name | Amount of MMA | Amount of XL* |
|---|---|---|
| PEG-PMMA (8:4)r | 8.0 mmol | 4 mol % |
| PEG-PMMA (8:5)r | 8.0 mmol | 5 mol % |

Note:
*The combined concentrations of MMA and PEG-MA.

TABLE 1.3

Feed Compositions for the Preparation of Drug-Loaded
{PEG-PMMA (DDL)n} Nanospheres

| Sample Name | Amount of MMA | Amount of XL* | Amount of Drug (1.05 mol %) (w/w) † |
|---|---|---|---|
| PEG-PMMA (PDL)a | 8.0 mmol | 4 mol % | 10.0 mg; 0.012 mmol |
| PEG-PMMA (ZDL)a | 8.0 mmol | 4 mol % | 10.0 mg; 0.0343 mmol |
| PEG-PMMA (PDL)r | 8.0 mmol | (4 mol %) | 10.0 mg; 0.012 mmol |
| PEG-PMMA (ZDL)r | 8.0 mmol | 4 mol % | 10.0 mg; 0.0343 mmol |

Note:
*The combined concentrations of MMA and PEG-MA.
† The combined weights of MMA, PEG-MA and XL.

Characterization of Nanospheres

The characterization of nanoparticulate formulations as dosage forms intended for use in medicine is very important. The determination of these properties is of great relevance for quality control as well as for evaluating the influence of process parameters on the resulting formulation. In addition to these pharmaceutical considerations, there is also the challenge of establishing a correlation between the physicochemical properties of the systems and their interaction with blood components and resulting site disposition.

Surface Morphology

The morphology of the nanospheres was investigated by observing the dried nanoparticles using SEM (JEOL; JSM-5300 Scanning Microscope). Before observation, the particles were either fixed on a double-sided sticky carbon tape (for freeze-dried samples), which was adhered to a sample stand, or cast to a sample stand and dried at room temperature (for wet samples i.e., before freeze-drying). Then, they were sputter coated with gold in a Denton Vacuum Inc. Desk II instrument (45 mA), and examined in the JSM-5300 SEM instrument at 15 kV. The average particle sizes of the nanospheres could also be roughly estimated from the SEM results.

Size and Size Distribution

Particle size and size distribution measurements of the nanospheres were performed by photon correlation spectroscopy using a Zetasizer® 3000 (Malvern Instruments, Southborough, Mass.). The measurement was performed at 25° C. at a 90° scattering angle, and it was recorded for 180 s for each measurement. The mean hydrodynamic diameter was generated by cumulative analysis. The dried nanospheres (10 mg) were re-suspended in filtered distilled water (3 mL) by vortexing for one minute on a touch mixer (Fisher Scientific, Model 231) and then sonicated for three minutes using a Sonics Vibracell™ Amplitude sonicator (Sonics & Materials, Inc.) before measurement.

FTIR Characterization

The structures of paclitaxel, 2-chloro-3-diacetylamino-1, 4-naphthoquinone (Zapp88), paclitaxel-loaded nanospheres, Zapp88-loaded nanospheres and representative blank/empty nanospheres were characterized by FT-IR using solid paclitaxel, Zapp88, blank and drug-loaded nanospheres samples. The IR spectra were obtained on a Nicolet Magna-IR 560 spectrometer and the samples recorded as KBr pellets.

In Vitro Availability Studies

Preparation of Standard Calibration Curve for Paclitaxel

To determine the amount of paclitaxel in each of the nanosphere formulation PEG-MMA (PDL)a and PEG-MMA (PDL)r using HPLC, a standard calibration curve was first developed as a reference, following a previously described method. The curve was obtained by preparing different concentrations of paclitaxel ranging from 0.25 μg/mL to 25 μg/mL in acetonitrile, then determining the peak area for each concentration by HPLC analysis and finally plotting the peak area against the known concentration. An average of two replicates was used. The mobile phase was acetonitrile and ammonium phosphate buffer (12.5 mM, pH 4.5) (60:40). The analysis was carried out on a C18 reverse-phase Zorbax (300SB) HPLC column (5 μm; 4.6×250 mm) using an HP Series 1100 system. The flow rate was 1.0 mL/min, column temperature was 38° C. and the retention time was 10.0 minutes. UV-visible detection was performed at 227 nm (17-19) using a HP photodiode-array (DAD) detector. The correlation coefficient of the calibration curve was greater than 0.99.

In Vitro Availability of Paclitaxel from the Nanospheres

Paclitaxel-loaded nanospheres (5 mg) were suspended in 10 mL of the release buffer solution (PBS; pH 7.4, ionic strength 0.16) in a 15-mL tube. A layer of 1-octanol (3 mL) was placed on top of the buffer layer and the tube was then clamped onto a Labquake® Shaker (Barnstead/Thermolyne) capable of 360° rotation. The sampling was carried out in triplicate for each sample. The temperature was maintained at 37° C. At predetermined time intervals, the 1-octanol layer was removed and replaced with 3 mL fresh 1-octanol. Out of the 3 mL 1-octanol layer removed, 10 μL was taken out, diluted in 990 μL acetonitrile (i.e., a 1:100 dilution) and filtered with 0.2 μm filter. The filtrate was analyzed by HPLC as described in the previous section. Quantitation was carried out according to the standard curve prepared above for paclitaxel.

Preparation of Standard Calibration Curve for Zapp88

To measure the amount of Zapp88 in each of the nanosphere formulation PEG-MMA (ZDL)a and PEG-MMA (ZDL)r using HPLC, a standard calibration curve was first developed. The analysis for Zapp88 was carried out following the same procedure that was used for paclitaxel with slight modifications. The standard curve was obtained by preparing different concentrations of Zapp88 ranging from 0.25 µg/mL to 25 µg/mL in acetonitrile, then determining the peak area for each concentration by HPLC analysis and finally plotting the peak area against the known concentration. An average of two replicates was used. The mobile phase was acetonitrile and ammonium phosphate buffer (12.5 mM, pH 4.5) (60:40). The analysis was carried out on a C18 reverse-phase Zorbax (300SB) HPLC column (5 µm; 4.6×250 mm) using HP Series 1100 system. The flow rate was 1.0 mL/min, column temperature was 38° C. and the retention time was 10.0 minutes. UV-visible detection was performed at 249 nm using a HP photodiode-array (DAD) detector. The correlation coefficient of the calibration curve was greater than 0.995.

However, before the HPLC detection could be carried out, the UV wavelength of maximum absorbance ($\lambda_{max}$) for Zapp88 was determined. Determination of $\lambda_{max}$ for Zapp88

Concentrations of 16 µg/mL and 20 µg/mL of Zapp88 in acetonitrile were prepared for the determination of $\lambda_{max}$ on an UV-2401PC, UV-VIS Recording Spectrophotometer from SHIMADZU. Zapp88 absorbed UV light at three different wavelengths: 271 nm, 249 nm and 198 nm ($\lambda_{max}$). The absorbance at 249 nm was selected as the detection wavelength for HPLC analysis for a number of reasons. First, acetonitrile, the main component of the mobile phase absorbs UV light at 190 nm and its cut-off wavelength for analyzing dissolved samples should be 5-10 nm above this specific absorption wavelength. Since $\lambda_{max}$ for Zapp88 falls within this cut-off window, it would be difficult to tell which absorption relates to Zapp88 and which one relates to acetonitrile if 198 nm is used as the detection wavelength for HPLC analysis. Also, the absorption band at 271 nm was too broad (i.e., the peak at the wavelength was not sharp) and if used could generate problems if other components of the system absorb at the same wavelength without being detected. Therefore, 249 nm was selected as the detection wavelength for HPLC so as to sidestep the aforementioned problems.

In Vitro Availability of Zapp88 from the Nanospheres

Zapp88-loaded nanospheres (5 mg) were suspended in 10 mL of the release buffer solution (PBS; pH 7.4, ionic strength 0.16) in a 15-mL tube. The tube was then clamped onto the tube shaker. The sampling was carried out in triplicate for each sample. The temperature was maintained at 37° C. At predetermined time intervals, 2 mL solution was taken out and replaced with 2 mL fresh buffer solution maintained at 37° C. The 2 mL solution that was removed was extracted with 400 µL of dichloromethane of which 100 µL was taken out, diluted in 900 µL acetonitrile (i.e., a 1:10 dilution) and filtered with 0.2 µm filter. The filtrate was analyzed by HPLC as described under the section for the preparation of the standard calibration curve for Zapp88. Quantitation was carried out according to the standard curve prepared above for Zapp88.

Determination of the Loading Capacity of Nanospheres

The determination was as reported previously (16) with the exception that the HPLC analysis was the same as used for the in vitro availability studies of the drug-loaded nanospheres described above. The nanospheres were hydrolyzed for greater than one month till all the loaded drug was released (each sample in triplicate). Then quantitiation of paclitaxel or Zapp88 was analyzed by a HPLC method as described above. The encapsulation property of the nanospheres was expressed as the loading capacity (amount of drug encapsulated expressed as a percentage of the nanospheres weight).

Results and Discussion

Scheme 1 shows the synthesis of the hydrolyzable crosslinked PEG-PMMA nanospheres. The synthesis of the polymeric nanospheres proceeded by the free radical dispersion polymerization of a hydrophilic macromonomer (poly (ethylene glycol) monomethyl ether monomethacrylate (PEG-MA)) and a hydrophobic comonomer (methyl methacrylate (MMA)) in a polar binary solvent system (ethanol: water). The mechanism for the formation of the polymeric nanospheres, synthesized by the macromonomer technique proceeds in two major stages: (a) nuclei formation and (b) nuclei growth.

At the start of the process, MMA, PEG-MA, crosslinker (XL) and initiator formed a homogeneous solution in the continuous phase. The initiator or the co-initiator system decomposes to form free radicals, which react with the monomer (MMA) molecules to form oligomers and also initiate the crosslinking polymerization. The oligomers would then continue to grow to a critical chain length at which they precipitate from the medium and form small crosslinked PMMA nuclei. The amphiphilic nature of PEG-MA would make its polymerizable methacrylate moiety extend into the organic phase and its PEG segment would be left in the aqueous phase. The crosslinking copolymerization of MMA, XL and the methacrylate moiety of PEG-MA occurs in the nuclei. This results in the aggregation between the nuclei and stabilization by the PEG-MA macromonomer occurring simultaneously. Stabilization of the particles (nuclei) by PEG-MA is achieved by its presence on their surfaces. Once the nuclei are fully stabilized, the number of the particles during the polymerization remains constant. Outside the crosslinked cores is a hydrophilic shell comprising long-chain PEG segments. Consequently, the nanospheres were found to be easily dispersible in water. The empty nanospheres were dialyzed in distilled water in order to remove unreacted monomers and initiator molecules after which they were freeze-dried and stored in vials at 4° C.

The yields of the nanospheres (the amount of nanospheres recovered as a percentage of the weight of initial feed composition) at different feed ratios of the monomer (MMA) to the crosslinker (XL) (MMA-XL) are as shown in Table 2. The highest percent yield of nanospheres was achieved at monomer to crosslinker (M:X) feed ratio of 12:1. This maximum percent yield obtained was about 45%. The low yield might be due to a low conversion of monomers.

TABLE 2

Percent Yield of Nanospheres for Different Monomer:Crosslinker Ratios

| Sample Name[†] | % Yield |
|---|---|
| PEG-PMMA (6:1)a | 4.3 |
| PEG-PMMA (6:2)a | 11.3 |
| PEG-PMMA (6:3)a | 14.4 |
| PEG-PMMA (6:4)a | 6.4 |
| PEG-PMMA (8:1)a | 43.2 |
| PEG-PMMA (8:2)a | 33.8 |
| PEG-PMMA (8:3)a | 17.6 |
| PEG-PMMA (8:4)a | 23.1 |
| PEG-PMMA (8:4)r | 7.4 |
| PEG-PMMA (8:5)r | 13.1 |
| PEG-PMMA (10:1)a | 30.0 |
| PEG-PMMA (10:2)a | 8.7 |
| PEG-PMMA (10:3)a | 3.2 |
| PEG-PMMA (10:4)a | 3.7 |
| PEG-PMMA (12:1)a | 44.7 |
| PEG-PMMA (12:2)a | 34.0 |
| PEG-PMMA (12:3)a | 39.5 |
| PEG-PMMA (12:4)a | 23.9 |
| PEG-PMMA (PDL)a | 6.1 |
| PEG-PMMA (PDL)r | 6.6 |

TABLE 2-continued

Percent Yield of Nanospheres for Different Monomer:Crosslinker Ratios

| Sample Name[†] | % Yield |
|---|---|
| PEG-PMMA (ZDL)a | 2.2 |
| PEG-PMMA (ZDL)r | 1.9 |

Morphology of the Nanospheres:

The formation of the nanospheres was confirmed by SEM analysis as shown in FIGS. 2, 3, and 12-15. The images show that well formed and fairly monodispersed nanospheres were obtained.

Figure 4:
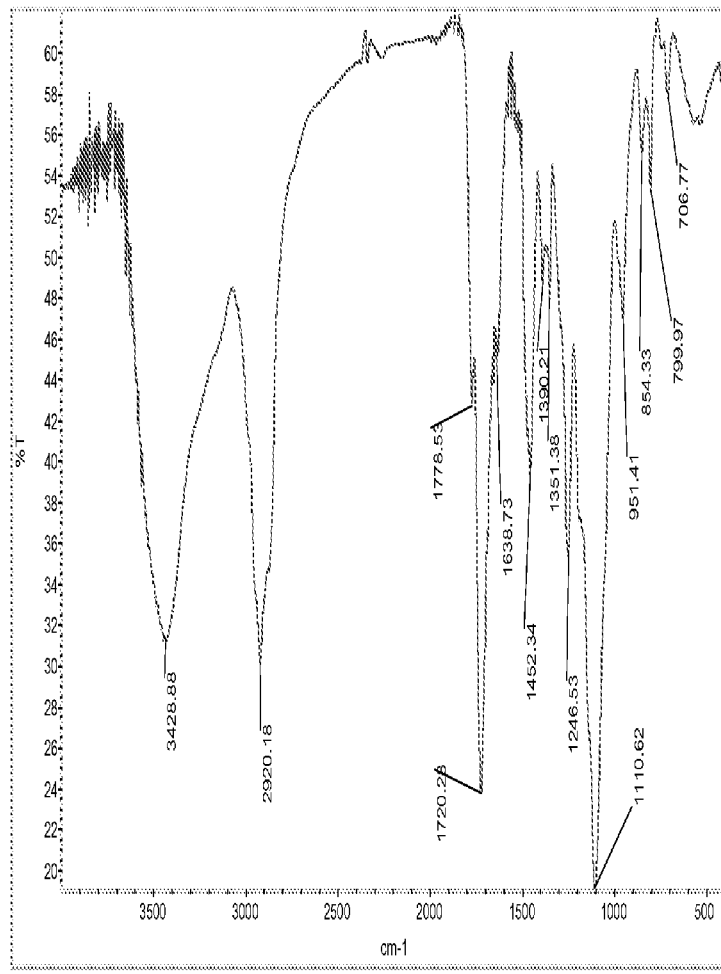
FIG. 4 is an IR spectrum of paclitaxel loaded hydrolyzable PEG-MMA nanospheres.
Figure 5:
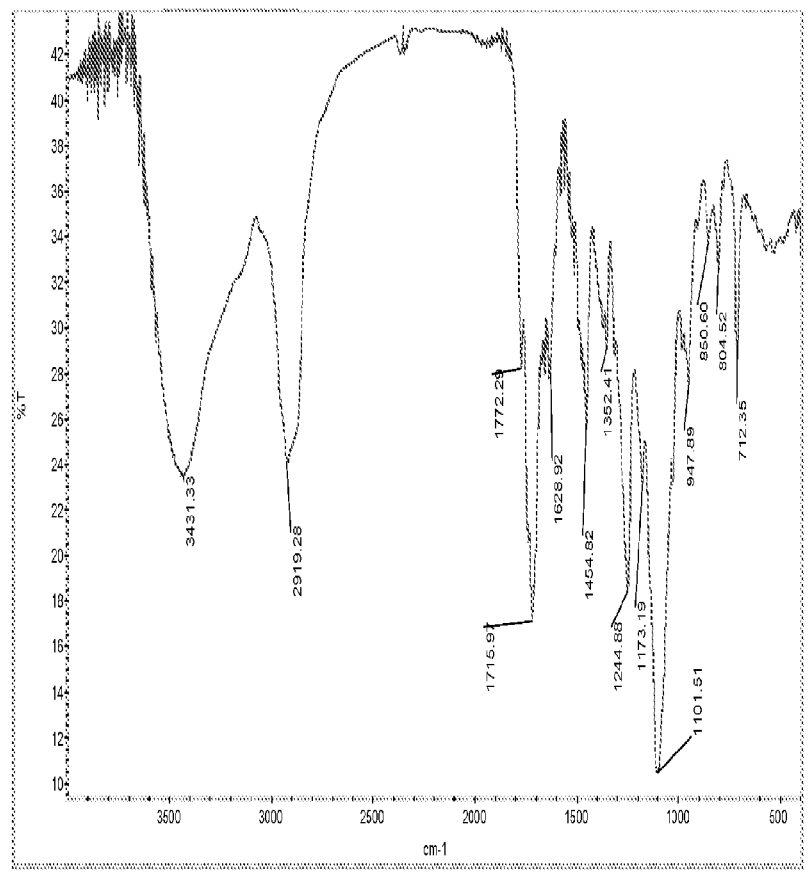
FIG. 5 is an IR spectrum of paclitaxel loaded hydrolyzable PEG-MMA (PDL)r nanospheres.
Figure 6:
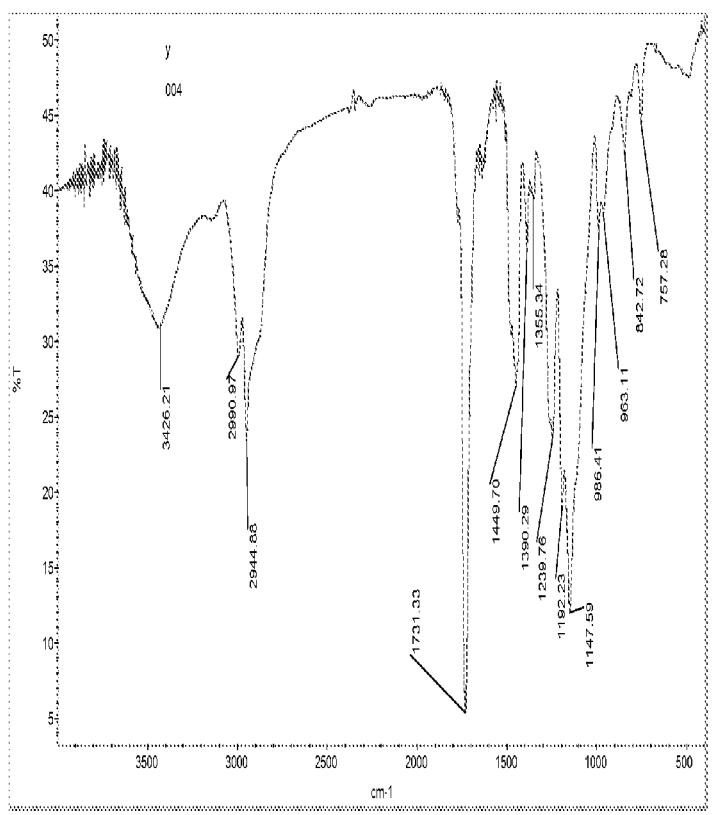
FIG. 6 is an IR spectrum of blank hydrolyzable PEG-MMA nanospheres (synthesized using AIBN as an intiator).

Structural Elucidation by FTIR Spectroscopy:

The data obtained on the FTIR analysis are shown in the Figures below. There were no significant differences between the IR spectra of the paclitaxel-loaded PEG-PMMA (PDL)a and PEG-PMMA (PDL)r nanospheres (FIGS. 4 and 5), so only the spectrum of the PEG-PMMA (PDL)r nanospheres (FIG. 5) would be used for discussion. Likewise, for the empty nanospheres, the IR spectra are virtually the same (FIGS. 6 and 7), therefore FIG. 7 (for PEG-PMMA (8:4)r nanospheres) will be used for discussion.

Figure 7:
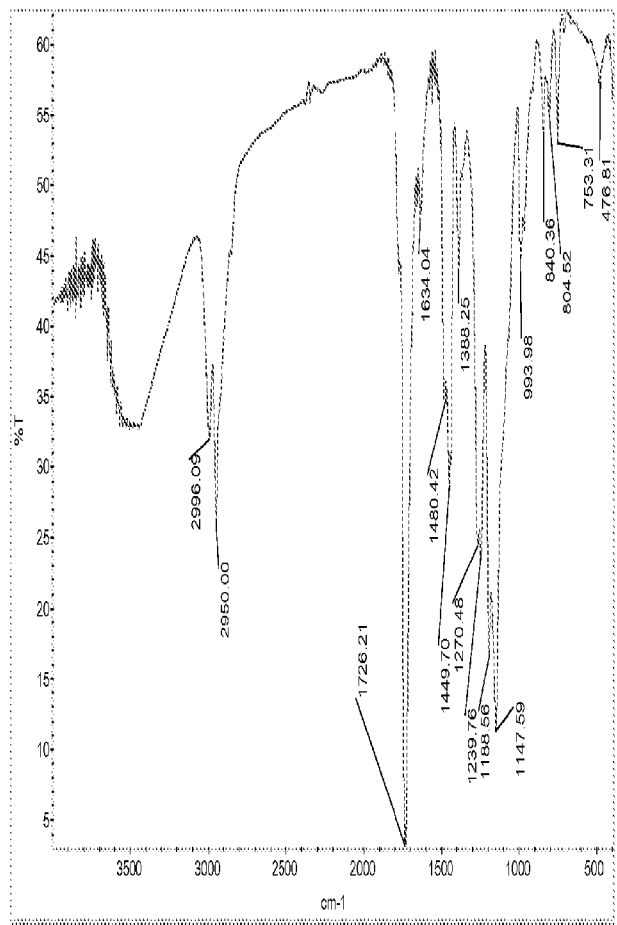
FIG. 7 is an IR spectrum of blank hydrolyzable PEG-MMA nanospheres (synthesized using organic redox system as an intiator).
Figure 8:
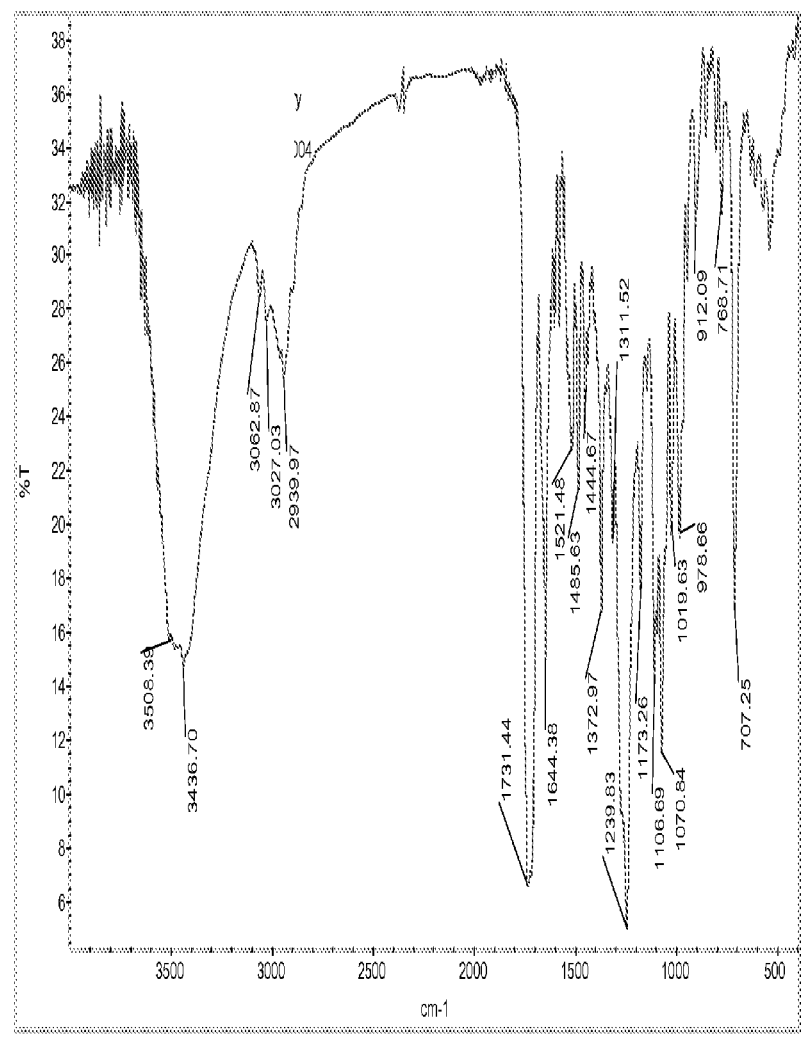
FIG. 8 is an IR spectrum of paclitaxel.

The IR of paclitaxel (FIG. 8) showed a strong OH stretching absorption at about 3500 $cm^{-1}$ and the ester (C=O) stretch at 1731 $cm^{-1}$. The amide C=O stretch in this molecule could be seen at 1644 $cm^{-1}$, while the C—O stretching absorption appeared at 1239 $cm^{-1}$. Once loaded into the nanospheres, these absorptions were not too prominent in the IR spectrum of the loaded nanospheres. However, there appeared to be two prominent changes in the IR spectrum of paclitaxel-loaded nanospheres (FIG. 5) when compared to that of the empty {PEG-PMMA (8:4)r} nanospheres (FIG. 7). The infrared spectrum of empty PEG-PMMA (8:4)r nanospheres showed a strong absorption at 1726 $cm^{-1}$ for the ester C=O stretching vibration, however, the paclitaxel-loaded PEG-PMMA (PDL)r nanospheres (FIG. 5) displayed relatively strong carbonyl absorption at 1715 $cm^{-1}$ instead. This shift in the C=O absorption to a lower wave number could have resulted from hydrogen bonding between the OH of paclitaxel and the carbonyl oxygen. Furthermore, it is likely that the presence of paclitaxel within the polymer core encouraged pockets for water molecules (which could not be removed after lyophilization) to hydrogen-bond. The IR of the loaded nanospheres displayed a strong broad band at about 3431 $cm^{-1}$ for the OH stretching vibration. Apparently, the incorporation of paclitaxel into the nanospheres appeared to have resulted in a structural morphology different from that of the empty nanospheres.

Figure 9:
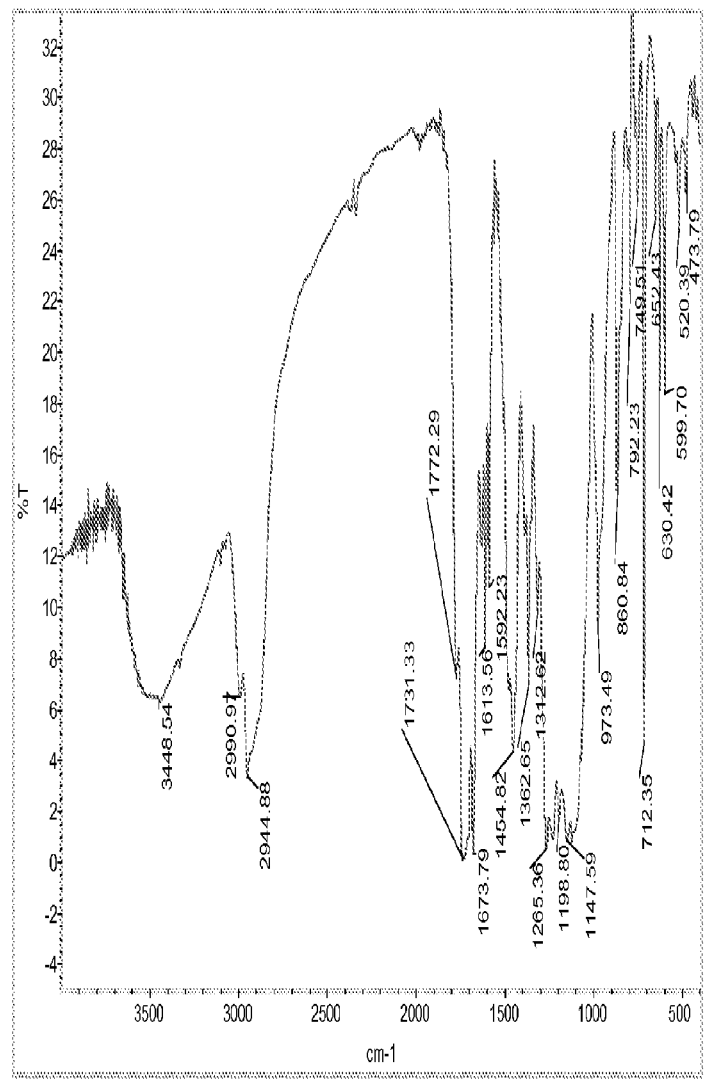
FIG. 9 is IR spectrum of 2-chloro-3-diacetylamino-1,4-naphthoquinone (Zapp88) loaded hydrolyzable PEG-MMA nanospheres.
Figure 10:
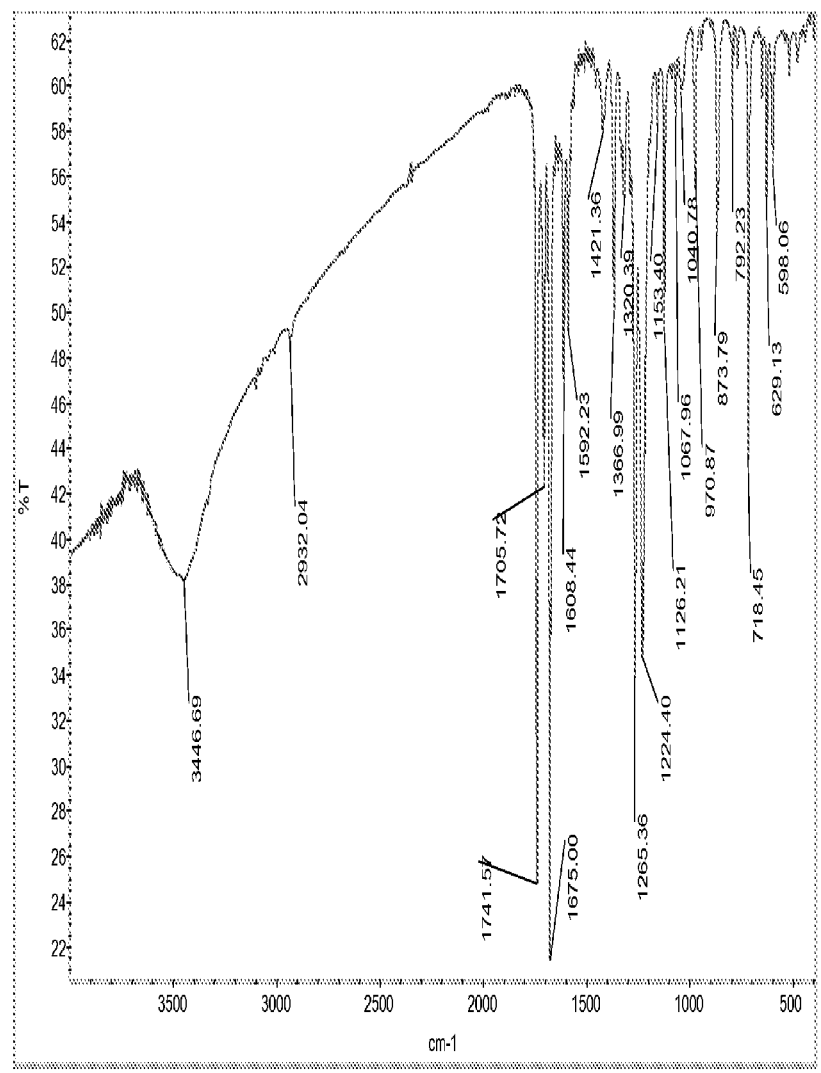
FIG. 10 is IR spectrum of 2-chloro-3-diacetylamino-1,4-naphthoquinone (Zapp88).
Figure 11:
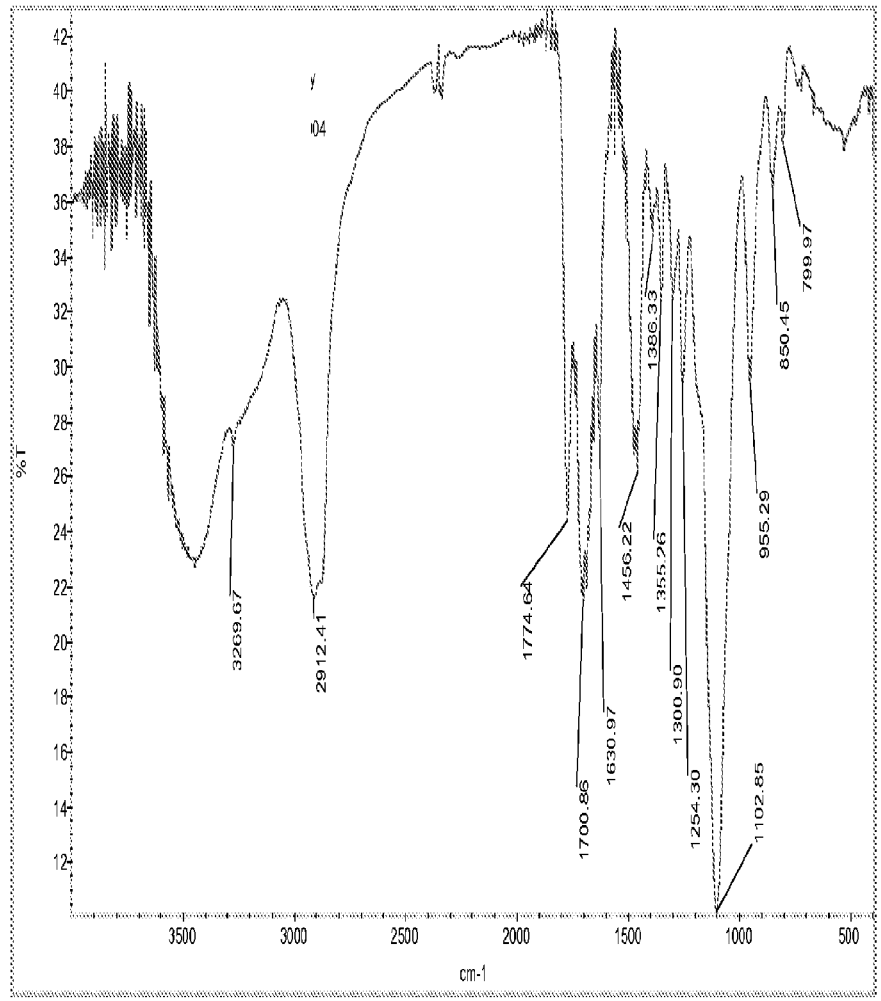
FIG. 11 is IR spectrum of 2-chloro-3-diacetylamino-1,4-naphthoquinone (Zapp88) loaded hydrolyzable PEG-MMA (ZDL)a nanospheres.
Figure 12:
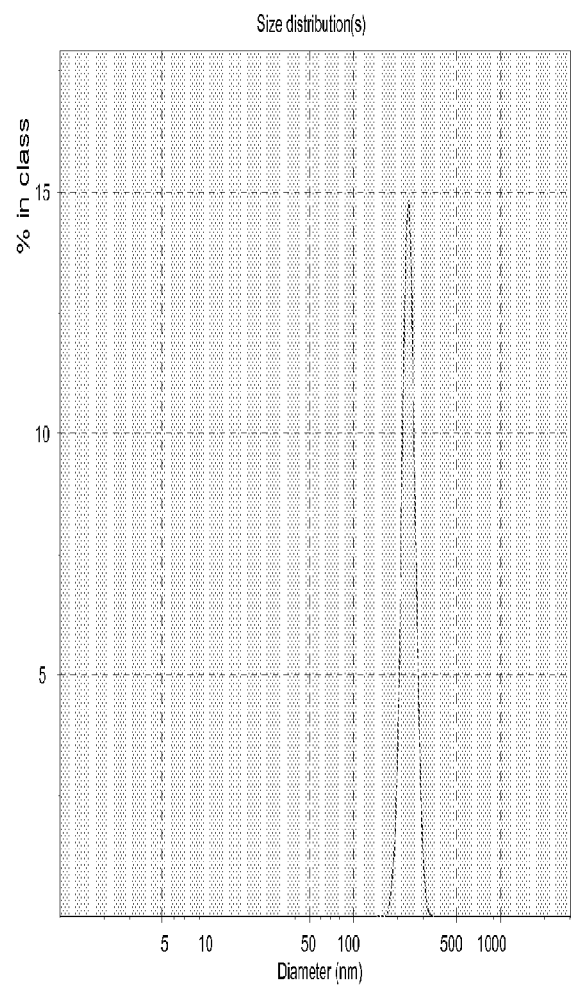
FIG. 12 is a particle size distribution diagram for PEG-MMA (6:3)a nanospheres.
Figure 13:
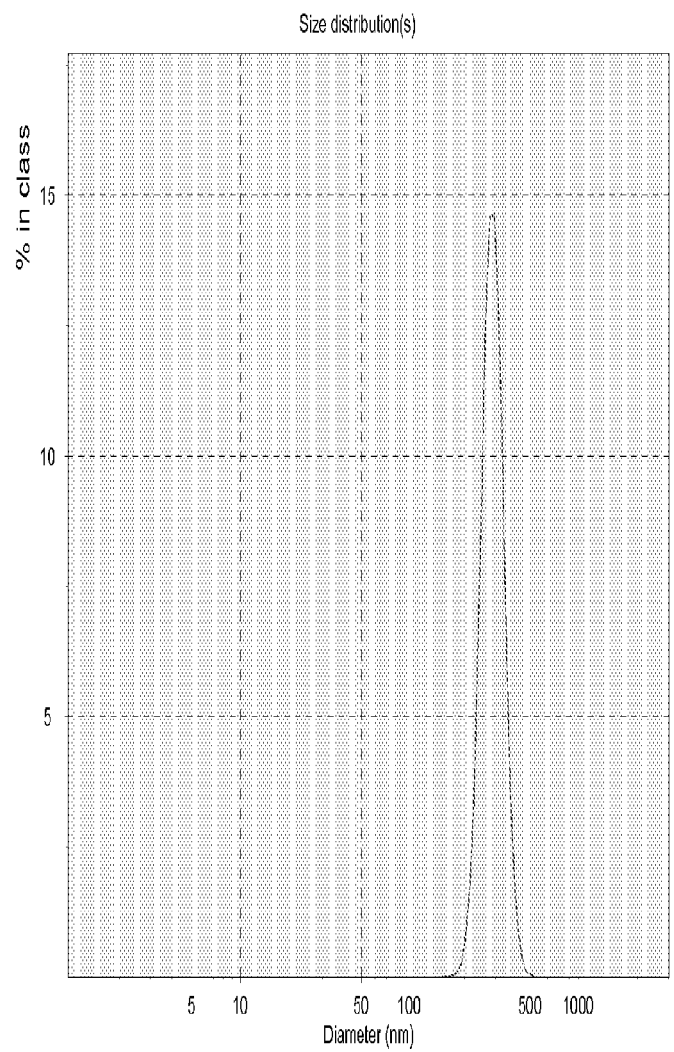
FIG. 13 is a particle size distribution diagram for PEG-MMA (10:4)a nanospheres.
Figure 14:
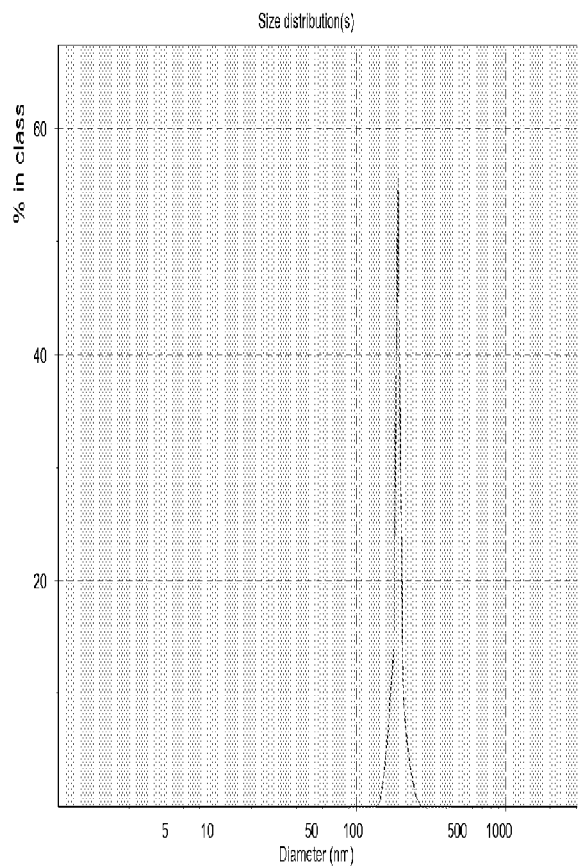
FIG. 14 is a particle size distribution diagram for PEG-MMA (8:4)r nanospheres.
Figure 15:
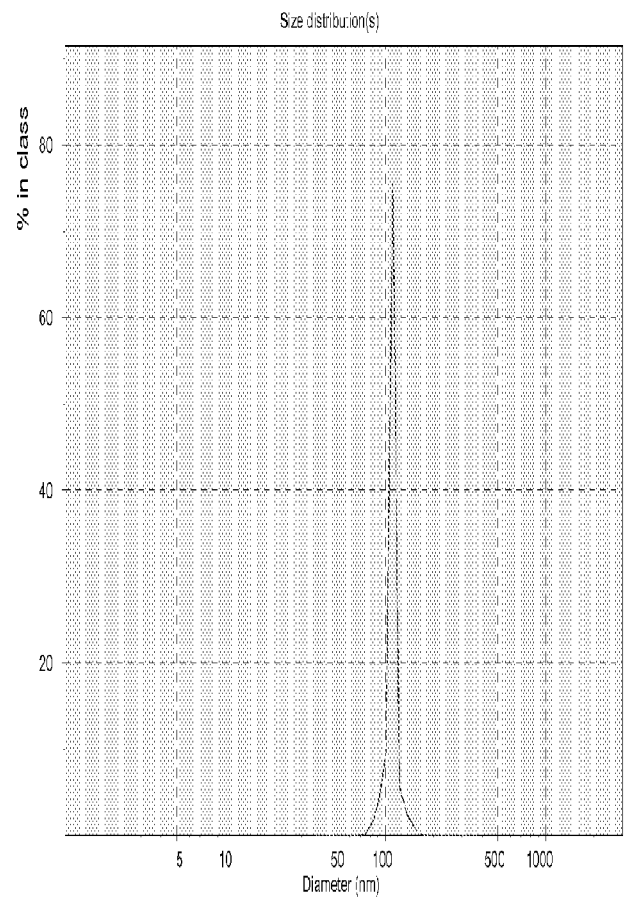
FIG. 15 is a particle size distribution diagram for PEG-MMA (8:5)r nanospheres.

On the other hand, the encapsulation of Zapp88 into the nanospheres resulted in the appearance of bands from the drug in the infrared spectrum of the Zapp88-encapsulated nanospheres PEG-PMMA (ZDL)r (FIG. 9). For instance, the C=O stretching vibration of the quinone could be seen at about 1674 $cm^{-1}$ and the C=C ring stretch could be seen at about 1613 $cm^{-1}$. The band at about 1731 $cm^{-1}$ in the nanospheres appears broader probably as a result of bands of 1741 $cm^{-1}$ and 1705 $cm^{-1}$ from Zapp88 (FIG. 10) overlapping with it. The infrared spectrum of Zapp88 is given in FIG. 10 for comparison. These results suggest that the smaller size of the Zapp88 molecule allowed more of it, compared to the amount of paclitaxel, to be encapsulated in the nanospheres network, and this reasoning is supported by the results obtained from the drug-loading and drug-release data discussed below.

Particle Size and Size Distribution

FIGS. 12 to 15 show the typical particle size distribution curves for the nanospheres synthesized. Tables 3.1 and 3.2 show the average particle sizes for the effect of variation in the amount of the monomer (MMA) and the crosslinker (XL) concentration. The size distributions illustrated in FIGS. 11 to 14 are narrow with the polydispersity ranging from 0.0103 to 0.507. This in agreement with the results obtained from the scanning electron micrographs, which also showed a narrow size distribution for the nanospheres.

A $4^n$ factorial experimental design was carried out to see the effect of monomer concentration (methyl methacrylate) and crosslinker concentration on the particle size. Number four indicates that each of the factors was examined at four levels (Table 3.1); while n=2 (two factors: methyl methacrylate and crosslinker concentration (Table 3.1). Analysis of variance for the factorial experimental design shows that the two factors (crosslinker concentration and the concentration of methylmethacrylate) are highly significant (i.e, they influence the particle size significantly); the interaction is also significant (i.e. the effect of one factor depends on the levels of the other factor) as shown in the response surface curve in FIG. 15.

TABLE 3.1

Average Particle Size Results for Nanospheres Fabricated with AIBN as Initiator

| Amount of MMA | Crosslinker Concentration (mmol %)[a]/ Average Particle Size (nm) | | | |
|---|---|---|---|---|
| (mmol) | 1 mol % | 2 mol % | 3 mol % | 4 mol % |
| 6.0 mmol | 431.6 nm | 333.3 nm | 219.0 nm | 176.2 nm |
| 8.0 mmol | 406.6 nm | 447.2 nm | 431.4 nm | 454.5 nm |
| 10.0 mmol | 411.6 nm | 364.4 nm | 254.0 nm | 144.4 nm |
| 12.0 mmol | 389.6 nm | 435.9 nm | 431.2 nm | 418.2 nm | mmol % - percent of the total amount of monomers (i.e., MMA and PEG-MA) in mmol

TABLE 3.2

Average Particle Size Results for Nanospheres Fabricated with REDOX Co-Initiators

| Amount of | Crosslinker Concentration (mmol %)/ Average Particle Size (nm) | |
|---|---|---|
| MMA (mmol) | 4 mol % | 5 mol % |
| 8.0 mmol | 185.4 nm | 95.9 nm |

Figure 16:
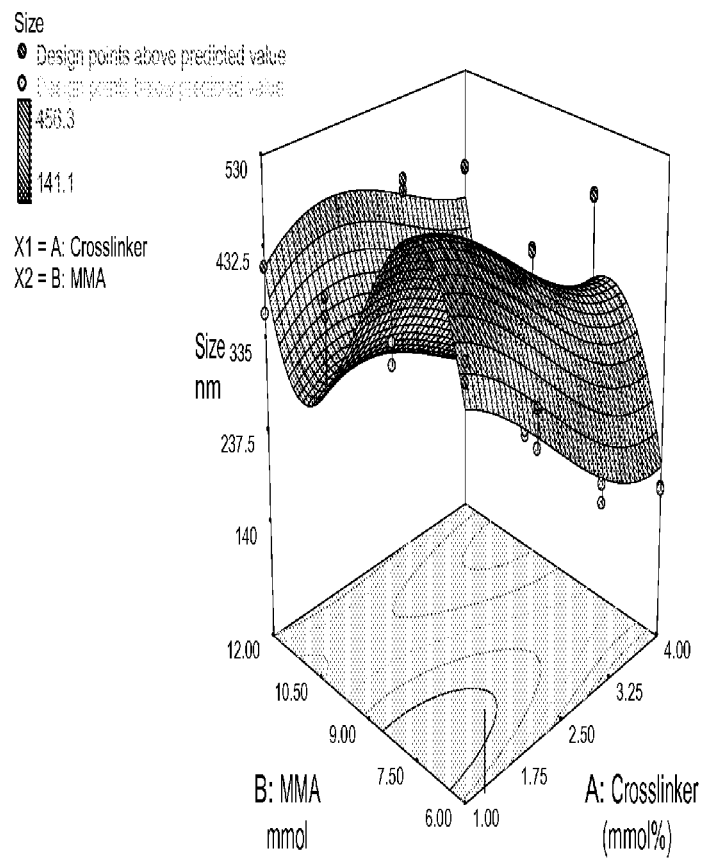
FIG. 16 is a response surface plot of the dependence of nanosphere particle size of methymethacrylate (MMA) and the crosslinker concentration, which is described by a cubic model obtained by nonlinear regression analysis.

From the data in Table 3.1, it can be seen that for the nanospheres prepared with either 6.0 or 10.0 mmol of MMA using AIBN as the initiator, increasing the amount of crosslinker resulted in a decrease in particle size. A similar behavior is seen with nanospheres prepared at two different levels of crosslinker concentration using the redox-initiated system (Table 3.2). This observation can be explained as follows: drug delivery systems based on polymeric micelles are generally not stable and drug release is often very fast. The block copolymer micelles are held together by van der Waals forces and need to be stabilized further. One way to achieve stability is to crosslink either the core or the shell of the micelles. The nanospheres studied in this work are core-crosslinked. Crosslinking typically results in a decrease in particle size of highly crosslinked particles. Therefore, the decrease in the particle sizes of the nanospheres as the crosslinker concentration increased was expected. However, the reverse is the case with nanospheres prepared with 8.0 and 12.0 mmol of MMA with increasing the amount of the crosslinker (Table 3.1 and FIG. 16). In this case, particle size appeared to have slightly increased with increase in crosslinker concentration: the effect of changes in the crosslinker concentration was not pronounced. Generally, the data shows that it is possible to achieve the desired particle size for a particular purpose by varying the formulation variables (namely the ratio of the monomer (MMA) to the crosslinker).

Drug-Loading Capacity

The drug loading experiments to determine the encapsulation efficiency of nanospheres containing paclitaxel and Zapp88 were carried out by incubating a known amount of drug-loaded nanospheres in a tube containing buffer (pH 7.4; ionic strength 0.16) for a month. After the incubation period, the drug released into the buffer medium was extracted with 1-octanol or methylene chloride for paclitaxel and Zapp88 respectively. The extracts were then analyzed by high performance liquid chromatography (HPLC) on a HP Series 1100 system equipped with a C18 reverse-phase Zorbax (300SB) HPLC column (5 µm; 4.6×250 mm) and a HP photodiode-array (DAD) detector. The encapsulation property of nanoparticles can be expressed as loading capacity (amount of drug encapsulated expressed as a percentage of the nanoparticles' weight) or as entrapment efficiency, which is the ratio of the quantity of the drug successfully encapsulated in the device versus that added in the preparation process. While drug loading can be expressed as loading capacity or encapsulation efficiency for nanoparticles fabricated from preformed polymers, loading capacity is appropriate for nanoparticle network(s) made by in situ polymerization like the nanospheres studied in this work. Therefore the loading capacity of the nanospheres studied were obtained using this formula:

$$\% \text{ Loading Capacity} = \frac{M_d}{M_n} \times 100$$

where $M_d$ is the weight of the drug (paclitaxel or Zapp88 in this case) in a known weight ($M_a$) of the nanosphere network.

TABLE 4

Loading Capacity of the Drug-Loaded {PEG-PMMA (DDL)n} Nanospheres

| Sample Name | % Loading Capacity |
|---|---|
| PEG-PMMA (PDL)a | 24.22 ± 0.85 |
| PEG-PMMA (PDL)r | 31.0 ± 2.22 |
| PEG-PMMA (ZDL)a | 6.78 ± 0.71 |
| PEG-PMMA (ZDL)r | 81.12 ± 7.19 |

Table 4 shows a summary of the drug-loading capacity of each drug-loaded nanosphere sample obtained in this study. As can be seen from the table, the percent drug-loading capacities of the nanospheres ranged from 6.78 to 81.12%. It appears that the paclitaxel-loaded nanospheres obtained from the redox-initiated polymerization reactions {PEG-PMMA (PDL)r} possess higher drug-loading capacities than those obtained from the AIBN-initiated reactions. The same observation is true of Zapp88-loaded nanospheres. This trend may be due to the higher solubility of the drugs in the polymerization medium at 60° C. for AIBN initiator system compared to 25° C. for the redox initiator system. The magnitude of the encapsulation efficiency for Zapp88 to paclitaxel in the nanospheres fabricated by redox-initiation is about 2.5 to 1. This implies that more Zapp88 compared to paclitaxel was encapsulated in the nanospheres probably due to the smaller size of the Zapp88 molecule. Further, preliminary solubility tests for both compounds showed that Zapp88 is more hydrophobic. This may make it partition more into the hydrophobic core of the nanospheres. These results are also in agreement with the IR data; where the bands of 1741 $cm^{-1}$ and 1705 $cm^{-1}$ from Zapp88 (FIG. 10) overlapped with the band at about 1731 $cm^{-1}$ in the drug-loaded nanospheres (FIG. 9), resulting in the band appearing broader.

The low drug-loading capacity of the PEG-MMA (ZDL)a nanospheres compared to the PEG-MMA (ZDL)r nanospheres is supported by their IR spectra (FIGS. 11 and 9); most of the signals attributed to the drug (especially to the aromatic region) are conspicuous in the spectrum of PEG-MMA (ZDL)r (FIG. 9) while they are not as apparent in the spectrum of PEG-MMA (ZDL)a (FIG. 11) probably due to low drug-loading capacity. It appears polymerization at high temperatures favors the diffusion of the drug from the hydrophobic core into the polymerization medium, resulting in low encapsulation efficiency.

In Vitro Drug Availability

Figure 17:
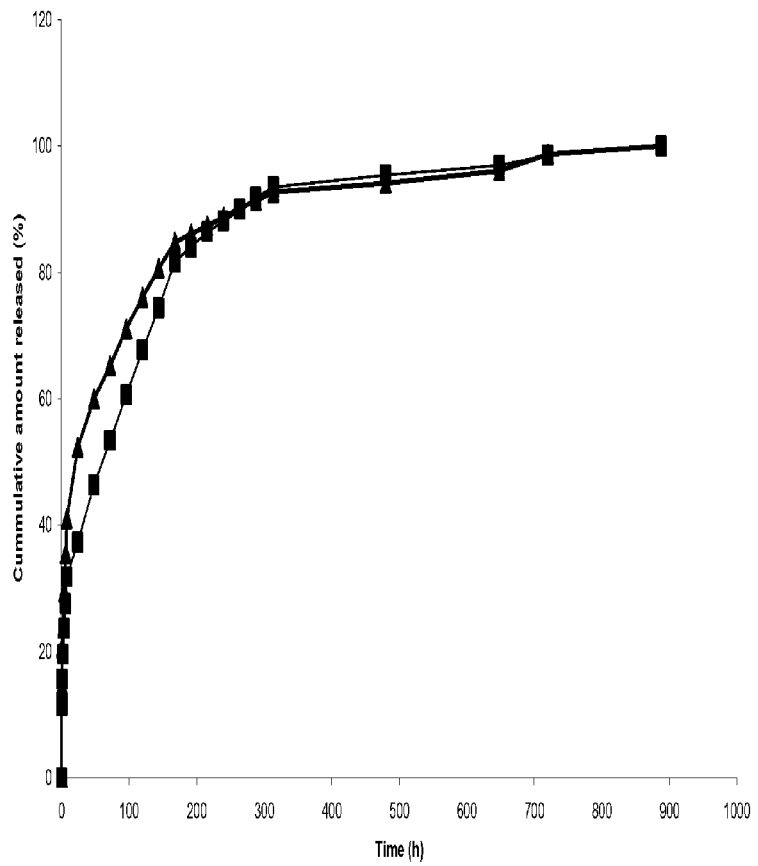
FIG. 17 is an in vitro release isotherm for paclitaxel loaded PEG-PMMA nanospheres prepared with different initiators (▲ Redox; ■ AIBN). Standard Deviation ε (0.011; 0.045).
Figure 18:
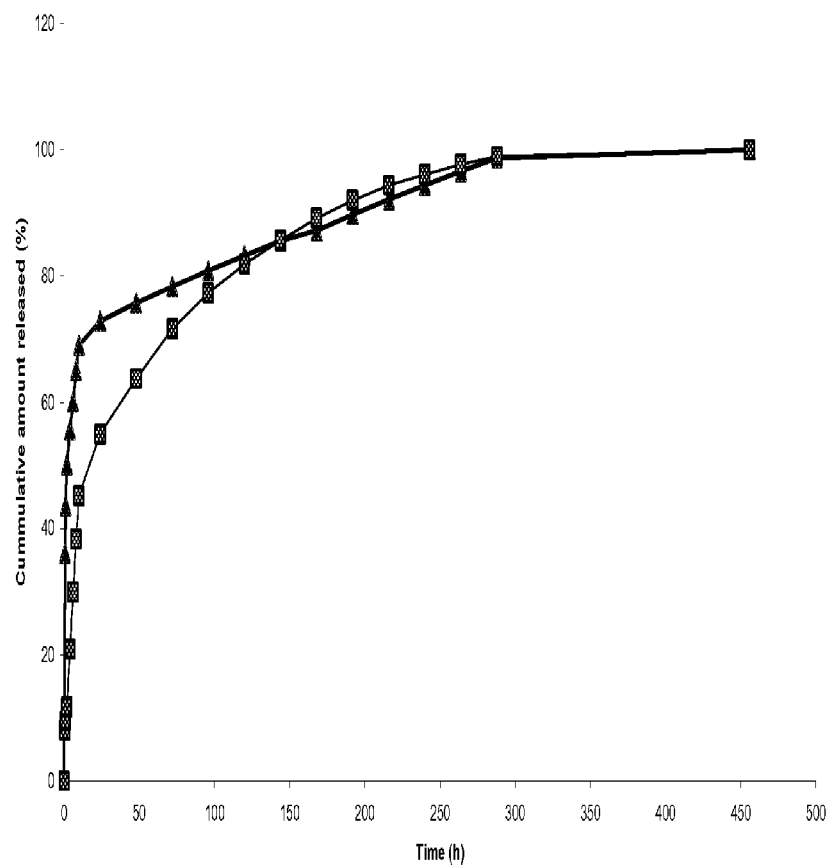
FIG. 18 is an in vitro release isotherm for Zapp88-loaded PEG-PMMA nanospheres prepared with different initiators (▲ Redox; ■ AIBN). Standard Deviation ε (0.009; 0.430).

FIG. 17 shows the release isotherms of the two paclitaxel-loaded stealth, hydrolyzable crosslinked nanospheres, while FIG. 18 shows the release isotherm of the two Zapp88-loaded nanospheres. The data show that the drug-loaded nanospheres sustained the release of the drugs though to different extents. The release is biphasic. There is an initial rapid release (burst effect) which may be due to the drug embedded on the surface (i.e., embedded on the free PEG tails of the stealth nanospheres) after the dispersion of the nanospheres in the release buffer solution. Akala and his coworkers studied a system of nanoparticles similar to the ones in this work. They prepared the nanoparticles by emulsion polymerization using AIBN as the initiator, PVA as the surfactant stabilizer and naltrexone (a narcotic antagonist) as the loaded drug. Similar burst effects were reported previously for nanoparticles prepared by emulsion polymerization; however, the magnitude of the burst effect was smaller in the nanospheres investigated in this work.

The release mechanism appears to be diffusion-controlled as the drug is made available slowly after the initial burst effect. Thus the drug release appears to be governed by the slow hydrolysis of the crosslinked core with the ingress of water or buffer molecules. The release profiles of these nanospheres are quite different from the release profiles of microspheres and nanospheres made from polyesters {e.g., poly (lactide-co-glycolide)} in which the release is triphasic: burst release phase followed by diffusion-controlled release phase and later degradation-controlled release phase in which the release is governed by polymer degradation (27).

Results show (FIGS. 17 and 18) that the release is faster and the duration of controlled release is shorter in Zapp88-loaded nanospheres (FIG. 18) than in paclitaxel-loaded nanospheres (FIG. 17). This observation can be attributed to the faster diffusion of lower molecular weight Zapp88 compared to the higher molecular weight paclitaxel. Another possible reason may be due to the effect of each drug on the hydrolysis of the crosslinked structure.

REFERENCES

1. Gaither, A., Lourgenko, V., RNA Interference Technologies and their Use in Cancer Research, *Curr. Opin. Oncol.*, 1950-54 (2007).
2. Cancer Nanotechnology (Going Small for Big Advances: Using Nanotechnology to Advance Cancer Diagnosis, Prevention and Treatment). U.S. Department of Health and Human Services, National Institutes of Health/National Cancer Institute. NIH Publication No. 04-5489,2004).
3. Eric M Pridgen, Robert Langer, Omid C Farokhzad Biodegradable, polymeric nanoparticle delivery systems for cancer therapy, *Nanomedicine*, 2(5), 669-80 (October 2007).
4. Minko, T., Dharap, S. S., Pakunlu, R. I., Wang, Y., Molecular Targeting of Drug Delivery Systems to Cancer, *Current Drug Targets*, 5, 389-406 (2004).
5. Pakunlu, R. I., Wang, Y., Tsao, William, Pozharov, V., Cook, T. J., Minko, T., Enhancement of the Efficay of Chemotherapy for Lung Cancer by Simultaneous Suppression of Multidrug Resistance and Antiapoptotic Cellular Defense: Novel Multicomponent Delivery System, *Cancer Research*, 64, 6214-6224 (2004).
6. Ferrari, M. Cancer Nanotechnology: Opportunities and Challenges, *Nature Reviews/Cancer*, 5; 1-11 (2005).
7. Nasongkla, Norased, Bey, Erik, Ren, Jimin, Ai, Hua, Khemtong, Chalermchai, Guthi, Jagadeesh Setti, Chin, Shook-Fong, Sheery, A. Dean, Boothman, David A. and Gao, Jinming, Multifunctional Polymeric Micelles as Cancer-Targeted, MRI-Ultasenstive Drug Delivery Sytems, *Nano Letters*, 6(11), 2427-2430 (2006).
8. Shenoy, D. B., Amiji, M. M., Poly(ethylene oxide)-modified poly(-caprolactone) Nanoparticles for Targeted Delivery of Tamoxifen in Breast Cancer, *Int. J. Pharm.*, 293, 261-70 (2005).
9. Yokoyama, M., Okano, T., Targetable Drug Carriers: Present Status and a Future Perspective, *Advanced Drug Delivery Reviews* 21, 77-80 (1996).
10. Cammas, S., Suzuki, K.; Sone, C.; Sakurai, Y., Kataoka, K., Okano, T, Thermo-Responsive polymer nanoparticles with a Core-Shell Micelle Structure as Site-Specific Drug Carriers, *Journal of Controlled Release* 48, 157-64 (1997).
11. Trail, P. A., Wilner, D., Lasch, S. J., Henderson, A. J., Hofstead, H., Casazza, A. M., Firestone, R. A., Hellstrom, K. E., Cure of Xenografted Human Carcinomas by BR96-Doxorubicin Immunoconjugatcs, *Science* 261, 212-15 (1993).
12. Lasic, D. D., Martin, F. J., Gabizon, A., Huang, S. K., Papahadjopoulos, D., Sterically Stabilized Liposomes: A Hypothesis on the Molecular Origin of the Extended Circulation Times, *Biochimica et Biophysica Acta (BBA)—Biomembranes* 1070, 187-92 (1991).
13. Huang, S. K., Stauffer, P. R., Hong, K., Uuo, J. W. H., Philips, T. L., Huang, A., Papahadjopoulos, D., Liposomes and Hyperthermia in Mice: Increased Tumor Uptake and Therapeutic Efficacy of Doxorubicin in Sterically Stabilized Liposomes, *Cancer Research* 54, 2186-91 (1994).
14. Bakare, O., Ashendel, C. L., Peng, H., Zalkow, L. H., Burgess, E. M., Synthesis of MEK1 Inhibitory Activities of Imido-Substituted 2-Chloro-1,4-naphthoquinones, *Bioorganic & Medicinal Chemistry* 11, 3165-70 (2003).
15. Bakare, O. and Copeland, R. (Departments of Chemistry and Pharmacology, Howard University, respectively: Unpublished Results).
16. Yin, W., Akala, E. O., Taylor, R. E., Design of Naltrexone-Loaded Crosslinked Nanoparticles, *International Journal of Pharmaceutics* 244, 9-19 (2002).
17. Xu, Q. A., Trissel, L. A., Stability-Indicating HPLC Methods for Drug Analysis. American Pharmaceutical Association: Washington, D. C. and Pharmaceutical Press: London (England), 1999.
18. Burm, J.-P., Jhee, S. S., Chin, A., Moon, Y. S. K., Jeong, E., Nii, L., Fox, J. L., Gill, M. A., Stability of Paclitaxel with Ondansetron Hydrochloride or Ranitidine Hydrochloride During Simulated Y-Site Administration, *American Journal of Hospital Pharmacy* 51, 1201-1204 (1994).
19. Longnecker, S. M., Donehower, R. C., Cates, A. E., Chen, T.-L., Brundrett, R. B., Grochow, L. B., Ettinger, D. S., Colvin, M., High-Performance Liquid Chromatography Assay for Taxol in Human Plasma and Urine and Pharmacokinetics in a Phase I Trial, *Cancer Treatment Reports* 71, 53-59 (1987).
20. Bamnolker, H., Margel, S., Dispersion Polymerization of Styrene in Polar Solvent: Effect of Reaction parameters on Microsphere Surface Composition and Surface Properties, Size and Size Distribution, and Molecular Weight, *Journal of Polymer Science: Part A: Polymer Chemistry* 34, 1857-71 (1996).
21. Kawaguchi, S., Winnik, M. A., Ito, K., Dispersion Copolymerization of n-Butyl Methacrylate with Poly(ethylene oxide) Macromonomers in Methanol-Water: Comparison of Experiment with Theory, *Macromolecules* 28, 1159-66 (1995).
22. Nugroho, M. B., Kawaguchi, S., Ito, K., Winnik, M. A, Control of Particle Size in Dispersion Polymerization Using Poly(ethylene oxide) Macromonomers, *Macromolecular Reports A*32, 593-601 (1995).
23. Rösler, A., Vandermeulen, W. M., Klok, H.-A., Advanced Drug Delivery Devices Via Self-Assembly of Amphiphilic Block Copolymers, *Advanced Drug Delivery Reviews* 53, 95-108 (2001).
24. Robinson, D. N., Peppas, N. A., Preparation and Characterization of pH-Responsive Poly(methacrylic acid-g-ethylene glycol) nanospheres, *Macromolecules* 35, 3668-74 (2002).
25. Feng, S.-S., Chien, S., Chemotherapeutic Engineering: Application and Further Development of Chemical Engineering Principles for Chemotherapy of Cancer and Other Diseases, *Chemical Engineering Science* 58, 4087-4114 (2003).
26. Akala, E. O., Kopečková, P., Kopeček, J., Novel pH-Sensitive Hydrogels with Adjustable Swelling Kinetics, *Biomaterials* 19, 1037-47 (1998).
27. Ramtoola, Z., Corrigan, O. I., Barrett, C. J., Release Kinetics of Fluphenazine from Biodegradable Microspheres, *Journal of Microencapsulation*, 9, 415-25 (1992).
28. Davis, B. K., Diffusion in Polymer Gel Implants, *Proceedings of the National Academy of Sciences of the United States of America* 71, 3120-23 (1974).

The invention claimed is:

1. A method of preparing polymer particles comprising the steps of
   (i) dissolving a reaction mixture of an acrylate, a poly (alkyleneglycol-graft-acrylate), an optionally hydrolysable crosslinking agent, and an initiator in a binary solvent system;
   (ii) heating the reaction mixture in an oxygen free atmosphere;
   (iii) leaving the reaction mixture to polymerize overnight in an oxygen free atmosphere, the polymerization being a free radical dispersion polymerization, wherein the free radical dispersion polymerization is performed at or below a temperature of about 25° C.; and,
   (iv) dialyzing in water.

2. The method of claim 1, wherein the binary solvent system is ethanol and water.

3. The method of claim 1, wherein the acrylate is methyl methacrylate (MMA).

4. The method of claim 1, wherein the poly(alkyleneglycol-graft-acrylate) is poly(ethyleneglycol-graft-methylmethacrylate).

5. The method of claim 3, wherein an amount of MMA used is from 6.0 to 12.0 mmol.

6. The method of claim 3, wherein an amount of MMA is 8.0 mmol, an amount of the hydrolysable crosslinking agent is from 4-5 mol %, and an amount of initiator is 1 mol %.

7. The method of claim 1, wherein the initiator is selected from the group consisting of benzoyl peroxide (BPO), N-phenyl diethanolamine (NPDEA), azo-bis-isobutyronitrile (AIBN), potassium persulfate (KPS), 2,2'-azobis-2,4-dimethylvaleronitrile (ADVN), PDMS macroazoinitiator (PDMS-azo), ammonium persulfate, thermal 2,2'-azobis[N-(2-carboxyethyl)-2-2-methylpropionamidine] (VA-057), amphoteric pH sensitive initiator, N,N-dimethyl-4-toluidine (DMT), N,N-dimethylbenzyl methacrylate, N,N-dimethylbenzyl alcohol, N,N-dimethylaniline, 4-N,N-dialkyl aminophenalkanoic acids and their methyl esters, peroxides, persulfate, peroxomonosulfate, peroxidiphosphate, metal ion oxidant-reducing agent systems, 2,2-dimethoxy-2-phenylacetophenone, Quantacure ITX photosensitizer and Irgacure 907 (I-907) initiator systems, and N,N-dimethyl ethanol amine.

8. The method of claim 7, wherein the initiator is a combination of BPO and NPDEA, used in a ratio of 50:50.

9. The method of claim 8, wherein an amount of poly (ethylene glycol)n monomethyl ether monomethacrylate (PEG-MA) used is 0.1 mmol.

10. The method of claim 8, wherein an amount of hydrolysable crosslinking agent used is from 0-4 mol % of a total volume of the reactants.

11. The method of claim 8, wherein the hydrolysable crosslinking agent is N,O-dimethylacryloylhydroxylamine.

12. The method of claim 7, wherein the initiator is azobisisobutyronitrile.

13. The method of claim 12, wherein an amount of azobisisobutyronitrile is 1 mol % of a total volume of the reactants.

14. The method of claim 12, further comprising a therapeutic agent in the reaction mixture.

15. The method of claim 14, wherein the therapeutic agent is selected from the group consisting of 2-chloro-3-diacetylamino-1,4-naphthoquinone, docetaxel, doxorubicin, and paclitaxel.

16. The method of claim 15, wherein the agent is paclitaxel.

17. The method of claim 4, wherein a polymerizable agent for preparing the optionally hydrolysable crosslinking agent is methacryloyl chloride.

18. A method of preparing polymer particles comprising the steps of:
providing a hydrophilic monomer selected from the group consisting of alkene glycol, polyalkylene glycol and mixtures thereof;
providing a hydrophobic acrylate monomer as copolymer;
providing a hydrolysable crosslinking agent; and
initiating polymerization to form the polymer particles using the hydrophilic monomer, the hydrophobic acrylate monomer, and the hydrolysable crosslinking agent via a free radical dispersion polymerization, wherein the free radical dispersion polymerization is performed at or below a temperature of about 25° C.

19. A method of preparing polymer particles comprising the steps of:
providing a compound represented by Formula (I):

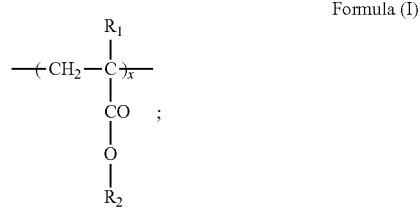

providing a compound represented by formula (II):

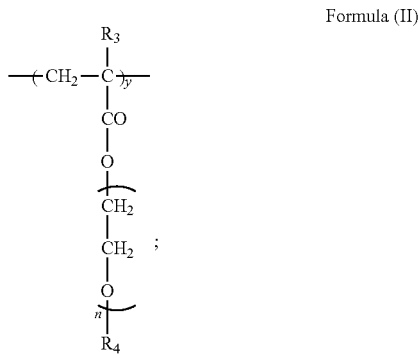

providing a compound represented by formula (III):

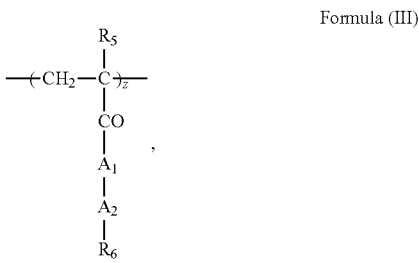

wherein $R_1$-$R_5$ each represent a group, which may be the same or different from each other, and the group is selected from the group consisting of a hydrogen, a halogen, and an alkyl group having one to five carbon atoms, wherein $R_6$ represents another chain of the crosslinked polymer particle comprised of structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine; and
initiating polymerization to form the polymer particles using the compounds of Formulas (I), (II), and (III) via a free radical dispersion polymerization, wherein the free radical dispersion polymerization is performed at or below a temperature of about 25° C.

20. A method of preparing a therapeutic agent encapsulated within polymer particles comprising the steps of:
(i) dissolving a reaction mixture of an acrylate, a poly (alkyleneglycol-graft-acrylate), an optionally hydrolysable crosslinking agent, and an initiator in a binary solvent system, the reaction mixture further comprising a therapeutic agent;
(ii) heating the reaction mixture in an oxygen free atmosphere;
(iii) leaving the reaction mixture to polymerize overnight in an oxygen free atmosphere, the polymerization being a free radical dispersion polymerization; and,
(iv) dialyzing in water.

* * * * *